US 7,507,718 B2

(12) United States Patent
Porro et al.

(10) Patent No.: US 7,507,718 B2
(45) Date of Patent: Mar. 24, 2009

(54) POLYMYXIN B ANALOGS FOR LPS DETOXIFICATION

(75) Inventors: Massimo Porro, Siena (IT); Massimo Velucchi, Arezzo (IT); Alessandro Rustici, Siena (IT); Monique Moreau, Lyons (FR); Noëlle Mistretta, Sain Bel (FR); Tino Krell, Huetor Vega (ES)

(73) Assignees: Sanofi Pasteur, Lyons Cedex (FR); Biosynth Srl, Rapolano Terme (Siena) (IT)

( * ) Notice: Subject to any disclaimer, the term of this patent is extended or adjusted under 35 U.S.C. 154(b) by 0 days.

(21) Appl. No.: 11/398,915

(22) Filed: Apr. 6, 2006

(65) Prior Publication Data

US 2006/0281684 A1 Dec. 14, 2006

Related U.S. Application Data

(60) Provisional application No. 60/697,121, filed on Jul. 7, 2005.

(30) Foreign Application Priority Data

Apr. 11, 2005 (EP) ................................. 05300270

(51) Int. Cl.
*A61K 38/08* (2006.01)
*A61K 38/10* (2006.01)

(52) U.S. Cl. .............................. 514/15; 514/13; 514/14; 514/16; 514/17

(58) Field of Classification Search ....................... None
See application file for complete search history.

(56) References Cited

U.S. PATENT DOCUMENTS

| 5,358,933 | A | | 10/1994 | Porro | |
|---|---|---|---|---|---|
| 5,652,211 | A | * | 7/1997 | Porro | ........................... 514/11 |
| 6,951,652 | B2 | * | 10/2005 | Porro | ....................... 424/234.1 |

FOREIGN PATENT DOCUMENTS

| EP | 0842666 A2 | 5/1998 |
|---|---|---|
| EP | 0976402 A2 | 2/2000 |
| WO | 93/14115 A1 | 7/1993 |
| WO | 95/03327 A2 | 2/1995 |
| WO | 96/38163 A1 | 12/1996 |
| WO | 2004/052394 A1 | 6/2004 |

OTHER PUBLICATIONS

Creighton, Proteins: Structure and Molecular Properties, 1984, W.H. Freeman and Co., New York, pp. 17-20.*
Rustici, Alessandro, et al., "Molecular Mapping and Detoxification of the Lipid A Binding Site by Synthetic Peptides," Science, Jan. 15, 1993, pp. 361-365, vol. 259.
Demitri, M.T., et al., "Inhibition of LPS-Induced Systemic and Local TNF Production by a Synthetic Anti-Endotoxin Peptide (SAEP-2)," Journal of Endotoxin Research, 1996, pp. 445-454, vol. 3, No. 6, Pearson Professional Limited.
Velucchi, Massimo, et al., "Molecular Requirements of Peptide Structures Binding to the Lipid-A Region of Bacterial Endotoxins" Vaccines, 1994, pp. 141-146, Cold Spring Laboratory Press.
Velucchi, Massimo, et al., "A Model of *Neisseria meningitidis* Vaccine Based on LPS Micelles Detoxified by Synthetic Anti-endotoxin Peptides," Journal of Endotoxin Research, 1997, pp. 261-272, Harcourt Brace & Company Limited.
Kloczewiak, Marek, et al., "Synthetic Peptides that Mimic the Binding Site of Horseshoe Crab Antilipopolysaccharide Factor," The Journal of Infectious Diseases, 1994, pp. 1490-1497, The University of Chicago.
Kohn, Fred R., et al., "Protective Effect of a Recombinant Amino-Terminal Fragment of Bactericidal/Permeability-Increasing Protein in Experimental Endotoxemia," The Journal of Infectious Diseases, 1993, pp. 1307-1310, The University of Chicago.
Marra, Marian N., et al., "The Role of Bactericidal/Permeability-Increasing Protein As A Natural Inhibitor of Bacterial Endotoxin," The Journal of Immunology, Jan. 15, 1992, pp. 532-537, vol. 148, No. 2, The American Association of Immunologists.
Stokes, Dennis C., et al., "Polymyxin B Prevents Lipopolysaccharide-Induced Release of Tumor Necrosis Factor-a from Alveolar Macrophages," The Journal of Infectious Diseases, Jul. 1989, pp. 52-57, vol. 160, No. 1, The University of Chicago.
Craig, William A., et al., "Prevention of the Generalized Shwartzman Reaction and Endotoxin Lethality by Polymyxin B Localized in Tissues," Infection and Immunity, Aug. 1974, pp. 287-292, vol. 10, No. 2, American Society for Microbiology.
Morrison, David C., et al., "Binding of Polymyxin B to the LIPID a Portion of Bacterial Lipopolysaccharides," Immunochemistry, Oct. 13, 1976, pp. 813-818, vol. 13, No. 10.
Massimo Porro. 1994, Structural Basis of Endotoxin Recognition by Natural Polypeptides, Trends in Microbiology 2(3): 65-66.

* cited by examiner

*Primary Examiner*—Cecilia Tsang
*Assistant Examiner*—Christina Marchetti Bradley
(74) *Attorney, Agent, or Firm*—McDonnell Boehnen Hulbert & Berghoff LLP

(57) ABSTRACT

The invention relates to SAEP II peptide dimers that mimic polymyxin B i.a. in its ability to bind non-covalently the lipopolysaccharide (LPS) of Gram-negative bacteria with high affinity, and therefore to detoxify LPS. The dimeric structure is maintained by a pair of disulphide bonds between two cystein residues present in the peptide sequence, which does not exceed 17 amino acids and essentially comprises cationic and hydrophobic amino acid residues. The peptides in the dimers may have a parallel or anti-parallel orientation. SAEP II dimers are useful for treating or preventing septic shock and related disorders generated by Gram-negative bacteria infection. The invention also relates to LPS-peptide complexes in which LPS and SAEP II diners are non-covalently bound together. These complexes are useful as vaccinal agents against Gram-negative bacteria infection.

77 Claims, 9 Drawing Sheets

Figure 1
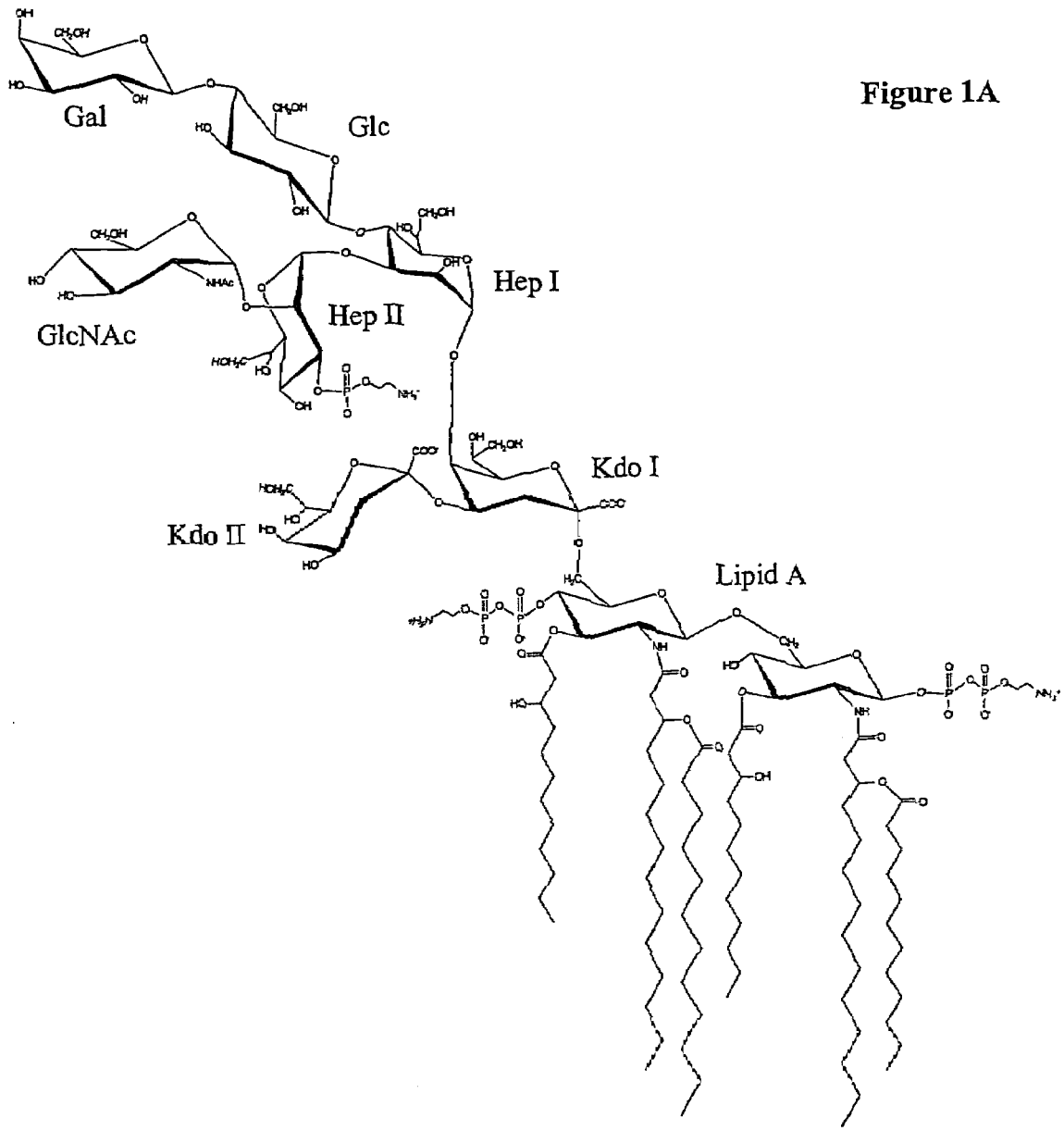
Figure 1A
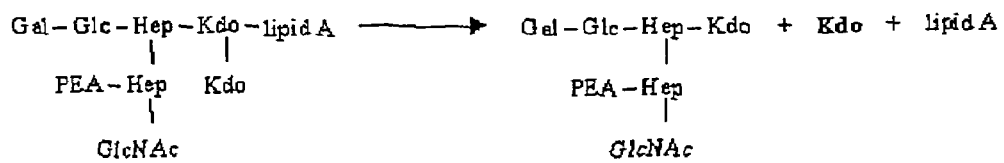
Figure 1B

Figure 5
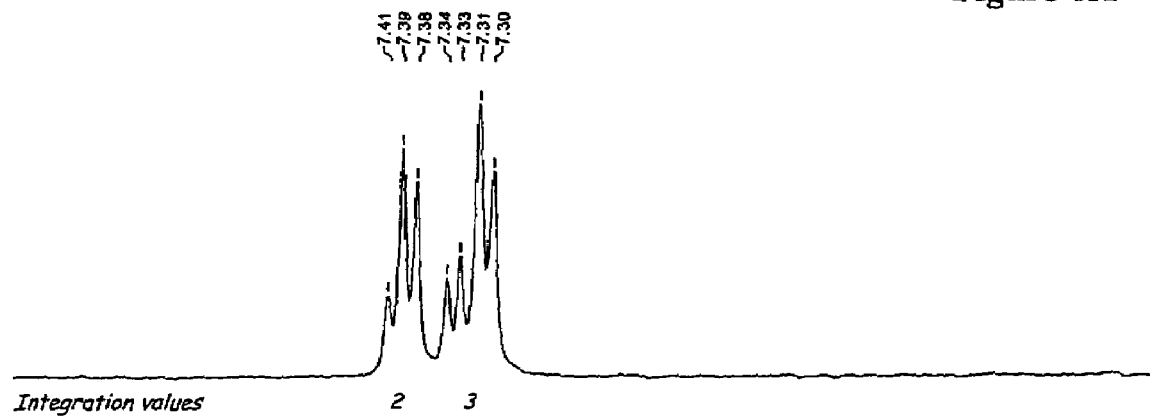
Figure 5A
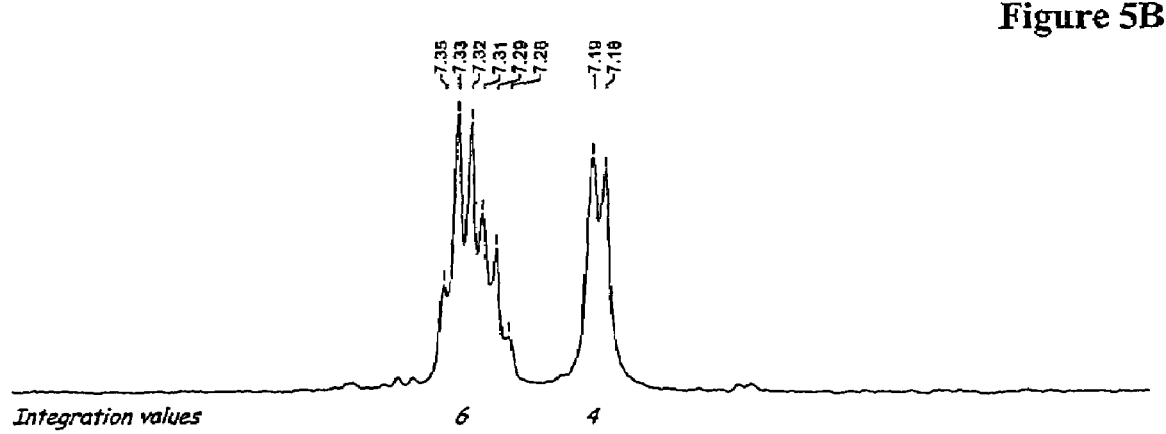
Figure 5B
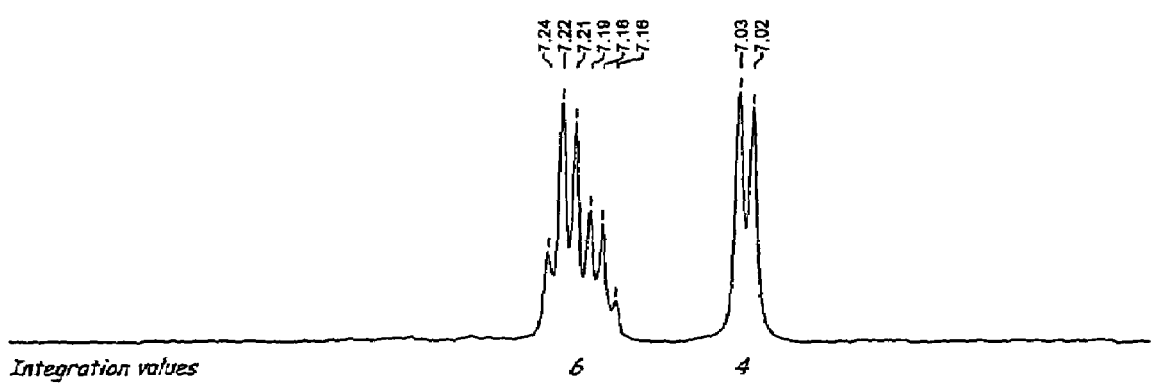
Figure 5C

```
                        SEQUENCE LISTING

<160> NUMBER OF SEQ ID NOS: 9

<210> SEQ ID NO 1
<211> LENGTH: 10
<212> TYPE: PRT
<213> ORGANISM: Artificial
<220> FEATURE:
<223> OTHER INFORMATION: Synthetic

<400> SEQUENCE: 1

Lys Thr Lys Cys Lys Phe Leu Lys Lys Cys
1               5                   10

<210> SEQ ID NO 2
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Any amino acid or optionally absent.
<220> FEATURE:
<221> NAME/KEY: misc_feature
<222> LOCATION: (2)..(2)
<223> OTHER INFORMATION: Any amino acid or optionally absent.
<220> FEATURE:
<221> NAME/KEY: misc_feature
<222> LOCATION: (3)..(3)
<223> OTHER INFORMATION: any amino acid or optionally absent.
<220> FEATURE:
<221> NAME/KEY: misc_feature
<222> LOCATION: (4)..(4)
<223> OTHER INFORMATION: Any amino acid, but when amino acids at
      positions 1-3 are absent, X is selected from Lys, Hyl, Arg, or
```

His.
<220> FEATURE:
<221> NAME/KEY: misc_feature
<222> LOCATION: (5)..(5)
<223> OTHER INFORMATION: Any amino acid, but when amino acids at
      positions 1-3 are absent, X is selected from Lys, Hyl, Arg, or
      His.
<220> FEATURE:
<221> NAME/KEY: misc_feature
<222> LOCATION: (7)..(7)
<223> OTHER INFORMATION: Any amino acid or optionally absent.
<220> FEATURE:
<221> NAME/KEY: misc_feature
<222> LOCATION: (8)..(8)
<223> OTHER INFORMATION: Any amino acid or optionally absent.
<220> FEATURE:
<221> NAME/KEY: misc_feature
<222> LOCATION: (9)..(9)
<223> OTHER INFORMATION: Any amino acid or optionally absent.
<220> FEATURE:
<221> NAME/KEY: misc_feature
<222> LOCATION: (10)..(10)
<223> OTHER INFORMATION: Any amino acid or optionally absent.
<220> FEATURE:
<221> NAME/KEY: misc_feature
<222> LOCATION: (11)..(11)
<223> OTHER INFORMATION: Any amino acid, but when amino acids at
      positions 7-10 are absent, X is selected from Val, Leu, Ile, Phe,
      Tyr, or Trp.
<220> FEATURE:
<221> NAME/KEY: misc_feature
<222> LOCATION: (12)..(12)
<223> OTHER INFORMATION: Any amino acid, but when amino acids at
      positions 7-10 are absent, X is selected from Val, Leu, Ile, Phe,
      Tyr, or Trp.
<220> FEATURE:
<221> NAME/KEY: misc_feature
<222> LOCATION: (13)..(13)
<223> OTHER INFORMATION: Any amino acid, but when amino acids at
      positions 7-10 are absent, X is selected from Val, Leu, Ile, Phe,
      Tyr, or Trp.
<220> FEATURE:
<221> NAME/KEY: misc_feature
<222> LOCATION: (15)..(15)
<223> OTHER INFORMATION: Any amino acid or optionally absent.
<220> FEATURE:
<221> NAME/KEY: misc_feature
<222> LOCATION: (16)..(16)
<223> OTHER INFORMATION: Any amino acid or optionally absent.
<220> FEATURE:
<221> NAME/KEY: misc_feature
<222> LOCATION: (17)..(17)
<223> OTHER INFORMATION: Any amino acid or optionally absent.

<400> SEQUENCE: 2

Xaa Xaa Xaa Xaa Xaa Cys Xaa Xaa Xaa Xaa Xaa Xaa Xaa Cys Xaa Xaa
1               5                   10                  15

Xaa

<210> SEQ ID NO 3
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Any amino acid or optionally absent.
<220> FEATURE:
<221> NAME/KEY: misc_feature
<222> LOCATION: (2)..(2)
<223> OTHER INFORMATION: Any amino acid or optionally absent.
<220> FEATURE:
<221> NAME/KEY: misc_feature
<222> LOCATION: (3)..(3)

```
<223> OTHER INFORMATION: Any amino acid or optionally absent.
<220> FEATURE:
<221> NAME/KEY: misc_feature
<222> LOCATION: (4)..(4)
<223> OTHER INFORMATION: Any amino acid, but when amino acids at
      positions 1-3 are absent, X is selected from Lys, Hyl, Arg, or
      His.
<220> FEATURE:
<221> NAME/KEY: misc_feature
<222> LOCATION: (5)..(5)
<223> OTHER INFORMATION: Any amino acid, but when amino acids at
      positions 1-3 are absent, X is selected from Lys, Hyl, Arg, or
      His.
<220> FEATURE:
<221> NAME/KEY: misc_feature
<222> LOCATION: (7)..(7)
<223> OTHER INFORMATION: Any amino acid or optionally absent.
<220> FEATURE:
<221> NAME/KEY: misc_feature
<222> LOCATION: (8)..(8)
<223> OTHER INFORMATION: Any amino acid or optionally absent.
<220> FEATURE:
<221> NAME/KEY: misc_feature
<222> LOCATION: (9)..(9)
<223> OTHER INFORMATION: Any amino acid or optionally absent.
<220> FEATURE:
<221> NAME/KEY: misc_feature
<222> LOCATION: (10)..(10)
<223> OTHER INFORMATION: Any amino acid or optionally absent.
<220> FEATURE:
<221> NAME/KEY: misc_feature
<222> LOCATION: (11)..(11)
<223> OTHER INFORMATION: Any amino acid, but when amino acids at
      positions 7-10 are absent, X is selected from Val, Leu, Ile, Phe,
      Tyr, or Trp.
<220> FEATURE:
<221> NAME/KEY: misc_feature
<222> LOCATION: (12)..(12)
<223> OTHER INFORMATION: Any amino acid, but when amino acids at
      positions 7-10 are absent, X is selected from Val, Leu, Ile,
      Phe, Tyr, or Trp.
<220> FEATURE:
<221> NAME/KEY: misc_feature
<222> LOCATION: (13)..(13)
<223> OTHER INFORMATION: Any amino acid, but when amino acids at
      positions 7-10 are absent, X is selected from Val, Leu, Ile, Phe,
      Tyr, or Trp.
<220> FEATURE:
<221> NAME/KEY: misc_feature
<222> LOCATION: (15)..(15)
<223> OTHER INFORMATION: Any amino acid or optionally absent.
<220> FEATURE:
<221> NAME/KEY: misc_feature
<222> LOCATION: (16)..(16)
<223> OTHER INFORMATION: Any amino acid or optionally absent.
<220> FEATURE:
<221> NAME/KEY: misc_feature
<222> LOCATION: (17)..(17)
<223> OTHER INFORMATION: Any amino acid or optionally absent.

<400> SEQUENCE: 3

Xaa Xaa Xaa Xaa Xaa Cys Xaa Xaa Xaa Xaa Xaa Xaa Xaa Cys Xaa Xaa
1               5                   10                  15

Xaa

<210> SEQ ID NO 4
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Any amino acid or optionally absent.
<220> FEATURE:
```

```
<221> NAME/KEY: misc_feature
<222> LOCATION: (2)..(2)
<223> OTHER INFORMATION: Any amino acid or optionally absent.
<220> FEATURE:
<221> NAME/KEY: misc_feature
<222> LOCATION: (3)..(3)
<223> OTHER INFORMATION: Any amino acid or optionally absent.
<220> FEATURE:
<221> NAME/KEY: misc_feature
<222> LOCATION: (4)..(4)
<223> OTHER INFORMATION: Any amino acid, but when amino acids at
      positions 1-3 are absent, X is selected from Lys, Hyl, Arg, or
      His.
<220> FEATURE:
<221> NAME/KEY: misc_feature
<222> LOCATION: (5)..(5)
<223> OTHER INFORMATION: Any amino acid, but when amino acids at
      positions 1-3 are absent, X is selected from Lys, Hyl, Arg, or
      His.
<220> FEATURE:
<221> NAME/KEY: misc_feature
<222> LOCATION: (7)..(7)
<223> OTHER INFORMATION: Any amino acid or optionally absent.
<220> FEATURE:
<221> NAME/KEY: misc_feature
<222> LOCATION: (8)..(8)
<223> OTHER INFORMATION: Any amino acid or optionally absent.
<220> FEATURE:
<221> NAME/KEY: misc_feature
<222> LOCATION: (9)..(9)
<223> OTHER INFORMATION: Any amino acid or optionally absent.
<220> FEATURE:
<221> NAME/KEY: misc_feature
<222> LOCATION: (10)..(10)
<223> OTHER INFORMATION: Any amino acid or optionally absent.
<220> FEATURE:
<221> NAME/KEY: misc_feature
<222> LOCATION: (11)..(11)
<223> OTHER INFORMATION: Any amino acid, but when amino acids at
      positions 7-10 are absent, X is selected from Val, Leu, Ile, Phe,
      Tyr, or Trp.
<220> FEATURE:
<221> NAME/KEY: misc_feature
<222> LOCATION: (12)..(12)
<223> OTHER INFORMATION: Any amino acid, but when amino acids at
      positions 7-10 are absent, X is selected from Val, Leu, Ile, Phe,
      Tyr, or Trp.
<220> FEATURE:
<221> NAME/KEY: misc_feature
<222> LOCATION: (13)..(13)
<223> OTHER INFORMATION: Any amino acid, but when amino acids at
      positions 7-10 are absent, X is selected from Val, Leu, Ile, Phe,
      Tyr, or Trp.

<400> SEQUENCE: 4

Xaa Xaa Xaa Xaa Xaa Cys Xaa Xaa Xaa Xaa Xaa Xaa Xaa Cys
1               5                   10

<210> SEQ ID NO 5
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Any amino acid or optionally absent.
<220> FEATURE:
<221> NAME/KEY: misc_feature
<222> LOCATION: (2)..(2)
<223> OTHER INFORMATION: Any amino acid or optionally absent.
<220> FEATURE:
<221> NAME/KEY: misc_feature
<222> LOCATION: (3)..(3)
<223> OTHER INFORMATION: Any amino acid or optionally absent.
<220> FEATURE:
```

```
<221> NAME/KEY: misc_feature
<222> LOCATION: (4)..(4)
<223> OTHER INFORMATION: Any amino acid, but when amino acids at
      positions 1-3 are absent, X is selected from Lys, Hyl, Arg, or
      His.
<220> FEATURE:
<221> NAME/KEY: misc_feature
<222> LOCATION: (5)..(5)
<223> OTHER INFORMATION: Any amino acid, but when amino acids at
      positions 1-3 are absent, X is selected from Lys, Hyl, Arg, or
      His.
<220> FEATURE:
<221> NAME/KEY: misc_feature
<222> LOCATION: (7)..(7)
<223> OTHER INFORMATION: Any amino acid or optionally absent.
<220> FEATURE:
<221> NAME/KEY: misc_feature
<222> LOCATION: (8)..(8)
<223> OTHER INFORMATION: Any amino acid or optionally absent.
<220> FEATURE:
<221> NAME/KEY: misc_feature
<222> LOCATION: (9)..(9)
<223> OTHER INFORMATION: Any amino acid or optionally absent.
<220> FEATURE:
<221> NAME/KEY: misc_feature
<222> LOCATION: (10)..(10)
<223> OTHER INFORMATION: Any amino acid or optionally absent.
<220> FEATURE:
<221> NAME/KEY: misc_feature
<222> LOCATION: (11)..(11)
<223> OTHER INFORMATION: Any amino acid, but when amino acids at
      positions 7-10 are absent, X is selected from Val, Leu, Ile, Phe,
      Tyr, or Trp.
<220> FEATURE:
<221> NAME/KEY: misc_feature
<222> LOCATION: (12)..(12)
<223> OTHER INFORMATION: Any amino acid, but when amino acids at
      positions 7-10 are absent, X is selected from Val, Leu, Ile, Phe,
      Tyr, or Trp.
<220> FEATURE:
<221> NAME/KEY: misc_feature
<222> LOCATION: (13)..(13)
<223> OTHER INFORMATION: Any amino acid, but when amino acids at
      positions 7-10 are absent, X is selected from Val, Leu, Ile, Phe,
      Tyr, or Trp.

<400> SEQUENCE: 5

Xaa Xaa Xaa Xaa Xaa Cys Xaa Xaa Xaa Xaa Xaa Xaa Xaa Cys
1               5                   10

<210> SEQ ID NO 6
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Hydroxylysine

<400> SEQUENCE: 6

Lys Arg His Xaa Cys Lys Arg Ile Val Leu Cys
1               5                   10

<210> SEQ ID NO 7
<211> LENGTH: 11
<212> TYPE: PRT
<213> ORGANISM: Artificial
<220> FEATURE:
<223> OTHER INFORMATION: Synthetic

<400> SEQUENCE: 7

Lys Arg His Cys Val Leu Ile Trp Tyr Phe Cys
```

```
                                    -continued 1               5                  10

<210> SEQ ID NO 8
<211> LENGTH: 10
<212> TYPE: PRT
<213> ORGANISM: Artificial
<220> FEATURE:
<223> OTHER INFORMATION: Synthetic

<400> SEQUENCE: 8

Lys Thr Lys Cys Lys Phe Leu Leu Leu Cys
1               5                  10

<210> SEQ ID NO 9
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Hydroxylysine

<400> SEQUENCE: 9

Xaa Arg His Lys Cys Phe Tyr Trp Val Ile Leu Cys
1               5                  10
```

POLYMYXIN B ANALOGS FOR LPS DETOXIFICATION

The present invention relates to peptide analogs of polymyxin B that are useful for LPS detoxification. In the pharmaceutical field, they may be used (i) as such i.a. to treat fatal disorders, such as septic shock, caused by Gram-negative bacteria infection; or (ii) non-covalently bound to LPS which is therefore detoxified; the complex thereof being useful as vaccinal agent against Gram-negative bacteria infection.

Lipopolysaccharide (LPS) is a major constituent of the outer membrane of the cell wall of Gram-negative bacteria. LPS is highly toxic in mammals, particularly humans and with regard of its biological activity has been called endotoxin. It is responsible for the effects deriving from endotoxicosis in septic shock, a life-threatening event that occurs upon acute infection (sepsis) by Gram-negative bacteria.

LPS structure is constituted by a lipid moiety, called Lipid A, covalently linked to a polysaccharide moiety.

Lipid A is responsible for the toxic effect of LPS, in particular through interaction with B-cells and macrophages. This interaction induces the secretion of pro-inflammatory cytokines. The inflammatory condition may reach the fatal state of endotoxic shock.

Lipid A is highly hydrophobic and anchors LPS in the outer layer of the bacterial cell wall. Lipid A is composed of (i) a conserved bis-phosphorylated dissaccharide region (most frequently, N,O-acyl beta-1,6-D-glucosamine 1,4'-bisphosphate) with (ii) fatty acids, that substitute various hydrogen atoms pertaining to the disaccharide hydroxyls. The number of the fatty acids and their composition are interspecies variable. As a matter of example, each of the two symmetric glucosamines (GlcN1 and GlcN2) of *Neisseria meningitidis* lipid A carries the following fatty acids: 2N—C14,3OH; Cl2; and 3O—Cl2,3OH.

The LPS polysaccharide moiety is constituted by carbohydrate chains, responsible for antigenicity. The carbohydrate chain structure is itself composed of (i) a conserved inner core called the KDO (2-keto, 3-desoxyoctulosonic acid) region bound to lipid A and (ii) a variable outer core bound to the KDO region, that is commonly defined as including various saccharides, and the first repeat unit (that may comprised up to ten saccharides) of (iii) the external O-specific chains In Gram-negative, non-enteric bacteria such as *Neisserias, Bordetellas, Haemophilus* and *Moraxellas*, the O-specific chains do not exist (what is defined as the first repeat unit is in fact not repeated). Therefore, the LPS of these bacteria are often referred to as lipooligosaccharide (LOS).

LPS is not only toxic but also highly immunogenic. In mammals, anti-LPS antibodies are induced during infection and carriage, and may be protective. In view of this, it has been already proposed to detoxify LPS and to use the detoxified form thereof in prophylaxis of Gram-negative bacterial infections and related diseases.

Several detoxification methods are already known. In particular, it is possible to detoxify LPS while using polymyxin B or more appropriately, peptide analogs thereof.

Polymyxin B is a molecule that binds Lipid A with high affinity so that LPS is significantly detoxified. When given therapeutically in animal models, polymyxin B can prevent septic shock However, polymyxin B is a polycationic antibiotic that may be somewhat toxic to humans because of its non-biodegradability and the consequent tendency to accumulate in the kidneys. Therefore, it is not recommended for use in prophylactic or therapeutic products.

To overcome this limitation, peptide analogs to polymyxin B have been developed. They do not retain the polymyxin B toxicity but merely mimic the primary and secondary structures of polymyxin B and bind lipid A at the same site as polymyxin B does, so that a LPS-peptide complex is formed. As a result, LPS is detoxified. Peptide analogs are in particular described in U.S. Pat. No. 5,358,933, WO 93/14115, WO 95/03327, WO 96/38163, EP 842 666 and EP 976 402. One of them, the cyclic monomer SAEP2 (synthetic anti-endotoxin peptide 2) of formula KTKCKFLKKC (SEQ ID: 1) has been more particularly studied (Rustici et al, 1993, Science 259: 361 and Velucchi et al, 1997, J. Endotox. Res. 4(4): 261).

It has now been found that the SAEP2 peptide as well as similar peptides including in their sequences a number of uncharged polar amino acids surrounded by two adjacent cysteine residues and counter-balanced by a short external tail made of cationic amino acids (hereinafter generically referred to as SAEP II peptides) are of particular interest when they are in dimeric form; the dimer being conformationally made and maintained by a pair of disulphide bonds between the cysteine residues. Indeed, SAEP II peptide dimers exhibit enhanced detoxification properties over the corresponding monomers.

Therefore, the invention relates to a SAEP II peptide dimer of formula (I)

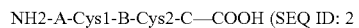
NH2-A-Cys1-B-Cys2-C—COOH (SEQ ID: 2)

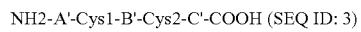
NH2-A'-Cys1-B'-Cys2-C'-COOH (SEQ ID: 3)

wherein the two Cys1 residues are linked together through a disulphide bond and the two Cys2 residues are linked together through a disulphide bond;

or formula (II)

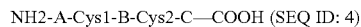
NH2-A-Cys1-B-Cys2-C—COOH (SEQ ID: 4)

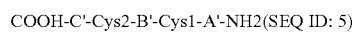
COOH-C'-Cys2-B'-Cys1-A'-NH2(SEQ ID: 5)

wherein the Cys1 residues are linked to the Cys2 residues through a disulphide bond;

wherein A and A' independently are a peptide moiety of from 2 to 5, preferably 3 or 4 amino acid residues, in which at least 2 amino acid residues, are independently selected from Lys, Hyl (hydroxy-Lysine), Arg and His;

wherein B and B' independently are a peptide moiety of from 3 to 7, preferably 4 or 5 amino acid residues, which comprise at least two, preferably three amino acid residues independently selected from Val, Leu, Ile, Phe, Tyr and Trp; and wherein C and C' are optional (these positions may be empty or not) and are independently an amino acid residue or a peptide moiety of from 2 to 3 amino acid residues;

provided that the cationic amino acid residues/hydrophobic amino acid residues ratio (cat/hydroph ratio) is from 0.4 to 2, advantageously from 0.5 to 1.2 or 1.5, preferably from 0.6 to 1; most preferably from 0.6 to 0.8; e.g. 0.75.

Advantageously, A and A' independently are a peptide moiety of from 2 to 5, preferably 3 or 4 amino acid residues, in which at least one, preferably 2 amino acid residues, are independently selected from Lys, Hyl, Arg and His; those that are not selected from Lys, Hyl, Arg and His ("the remaining amino acid residues"), if any, being selected from the group consisting of uncharged polar or nonpolar amino acids residues; preferably Thr, Ser and Gly; most preferably Thr.

When the A and A'peptide moieties comprise 3 amino acid residues, each of them can be a cationic residue; or alternatively, two out of three residues are cationic amino acids, whereas the remaining residue is selected from the group consisting of uncharged polar or nonpolar amino acids residues; preferably Thr, Ser and Gly; most preferably Thr.

When the A and A' peptide moieties comprise 4 amino acid residues, it is preferred that two or three out of four residues be selected from the groups of cationic amino acid residues as defined above, whereas the remaining residue (s) is (are) selected from the group consisting of uncharged polar or non-polar amino acids residues as defined above.

When the A and A' peptide moieties comprise 5 amino acid residues, it is preferred that three or four out of five residues be selected from the groups of cationic amino acid residues as defined above, whereas the remaining residue (s) is (are) selected from the group consisting of uncharged polar or non-polar amino acids residues as defined above.

Advantageously, B and B'independently are a peptide moiety of from 3 to 7, preferably 4 or 5 amino acid residues, which comprises at least two, preferably three amino acid residues independently selected from Val, Leu, Ile, Phe, Tyr and Trp; preferably from Leu, Ile and Phe; those that are not selected from Val, Leu Ile, Phe, Tyr and Trp ("the remaining amino acid residues"), if any, being independently selected from the group consisting of Lys, Hyl, Arg and His. As may be easily understood, the B and B' peptide moieties may comprise up to 7 amino acid residues independently selected from Val, Leu, Ile, Phe, Tyr and Trp. Advantageously, the B and B' peptide moieties comprise the sequence -X1-X2 -X3-, in which X1 and X2; X2 and X3; or X1, X2 and X3 are independently selected from Val, Leu, Ile, Phe, Tyr and Trp; preferably from Leu, Ile and Phe. In a preferred embodiment, the sequence -X1-X2-X3- comprises the Phe-Leu motif.

Particular embodiments of peptide moieties B and B' include:
(i) the -X1-X2-X3- sequence in which:
   X1 is Lys, Hyl, His or Arg, preferably Lys or Arg; more preferably Lys;
   X2 is Phe, Leu, Ile, Tyr, Trp or Val; preferably Phe or Leu; more preferably Phe; and
   X3 is Phe, Leu, Ile, Tyr, Trp or Val; preferably Phe or Leu; more preferably Leu; and
(ii) amino acid residues, if any, each being independently selected from the group consisting of Val, Leu, Ile, Phe, Tyr, Trp, Lys, Hyl, Arg and His; preferably Val, Leu, Ile, Phe, Tyr and Trp; more preferably Leu, Ile and Phe.

When B and B' comprise more than 4 nonpolar amino acid residues, A and A' preferably comprises at least 3 positively charged amino acid residues.

In the C and C' peptides moieties, the amino acid residue(s) may be any amino acid residues provided that the cationic amino acid residues/hydrophobic amino acid residues ratio remains within the specified range. Advantageously, they are independently selected from uncharged amino acid residues polar or nonpolar, these latter being preferred. However, in a preferred manner, C and C' are empty positions.

Therefore, a preferred class of dimers are of formula (III)

NH2-A-Cys1-B-Cys2-COOH(SEQ ID: 2)

NH2-A'-Cys1-B'-Cys2-COOH(SEQ ID: 5)

or formula(IV)

NH2-A-Cys1-B-Cys2-COOH(SEQ ID: 4)

HOOC-Cys2-B'-Cys1-A'-NH2(SEQ ID: 5)

wherein A, A', B and B' are as described above; provided that the cationic amino acid residues/hydrophobic amino acid residues ratio is from 0.4 to 2, advantageously from 0.5 to 1.2 or 1.5, preferably from 0.6 to 1; most preferably from 0.6 to 0.8; e.g. 0.75.

Dimers of formula (I) or (III), that is with peptides in the parallel orientation, are referred to as parallel dimers. Dimers of formula (II) or (IV), that is with peptides in the anti-parallel orientation, are referred to as antiparallel dimers.

In formulas (I) to (IV), A and A' are preferably identical. The same holds true for B and B'; and C and C'. A peptide dimer of formula (I), (II), (III) or (IV), in which A and A'; B and B'; and C and C' are two-by-two identical, is referred to as homologous dimer. Indeed, in this case, the peptide subunits included in the dimer are identical.

As a matter of example, the following peptides are cited as being suitable for use in dimers of the invention:

NH$_2$-Lys-Arg-His-Hyl-Cys-Lys-Arg-Ile-Val-Leu-Cys-COOH(SEQ ID: 6);

NH$_2$-Lys-Arg-His-Cys-Val-Leu-Ile-Trp-Tyr-Phe-Cys-COOH(SEQ ID: 7);

NH$_2$-Lys-Thr-Lys-Cys-Lys-Phe-Leu-Leu-Leu-Cys-COOH(SEQ ID: 8); and

NH$_2$-Hyl-Arg-His-Lys-Cys-Phe-Tyr-Trp-Val-Ile-Leu-Cys-COOH(SEQ ID: 9).

The respective cat/hydroph ratio of the corresponding homologous dimers are 2.00, 0.50, 0.75 and 0.67.

A particular example of the dimers described above, is constituted by a peptide of formula (V) NH2-Lys-Thr-Lys-Cys1-Lys-Phe-Leu-Leu-Leu-Cys2-COOH(SEQ ID: 8). This peptide is hereinafter referred to as the SAEP2-L2 peptide. As described above, it can also be in parallel or anti-parallel dimeric form.

Peptides involved in the or dimers of the invention can be conventionally synthesized by classical methods using e.g. a computer-driven automatic synthesizer. It is within the skills of professional practitioners in the art of peptide synthesis to know how to design procedures so that a particular peptide is obtained. It goes without saying that during the synthesis phase, the cysteine thiol groups can be protected. Once the synthesis is completed, they are de-protected and oxidation of the thiol groups is achieved in order to generate the cyclic monomer, the parallel or anti-parallel dimer.

When both cysteine residues present in the peptide are de-protected simultaneously, it is theoretically possible to generate each of the three forms upon oxidation. Then each of the three forms can be separated from each other by conventional biochemical purification methods. Preparative reverse-phase high performance liquid chromatography (RP-HPLC) is cited as a suitable example. Indeed, one may expect that each of the three forms elutes at a different retention time. Therefore, a preparation containing the purified cyclic monomer, or the purified parallel and anti-parallel dimers can be simply obtained by pooling together the respective peak fractions.

The respective proportions of each of the three forms generated upon oxidation depend on i.a. the specific amino acid sequence and importantly, the concentration of the peptide. It may happen that one or two of the three forms be predominantly created and indeed, the prevalence of one or two forms may be such that the other(s) are not formed at all.

As a matter of example, the SAEP2-L2 peptide spontaneously oxidises into cyclic monomer and anti-parallel dimer, in proportions, which depend from the concentration of the peptide in solution. The internal steric hindrance of the "side-chains" (the NH2-Lys-Thr-Lys-portion) of the anti-parallel dimer is obviously lower than that of the parallel dimer and one may expect that a lower minimal energy be responsible for the privileged formation of the anti-parallel dimer in aqueous solvents by comparison with the parallel dimer. As a direct consequence of this concentration-driven process, the formation of the anti-parallel dimer and to a lesser extent the cyclic monomer is favoured up to the exclusion of the parallel dimer from the equilibrium When the parallel dimer cannot be spontaneously generated upon oxidation, it is necessary to adopt particular measures to make the peptide associate within the parallel orientation. These measures are within the skills of the professional practitioners in the art of peptide synthesis. Nevertheless and as a matter of example only, it is indicated that differential protection of the Cys1 and Cys2 amino acids followed by selective de-protection is a convenient way to achieve dimerisation with the parallel orientation. Then the dimer may be purified by conventional methods, including RP-B: HPLC.

Peptides that are chemically synthesized and purified are commonly obtained in salt form due to the fact that acids and salts are used during the chemical synthesis and purification steps. Acetate is a salt commonly used. Therefore, it shall be understood that the term "peptide" as used in the present description encompasses the salt form as well.

Peptides for use in the dimers of the invention can be characterized by various techniques, including i.a. Ion Cyclotron Resonance (ICR), Mass Assisted Laser Desorption Ionisation—Time of Flights (MALDI-ToF) spectrometry and Nuclear Magnetic Resonance (NMR) spectrophotometry. In particular, it is possible to discriminate each of the three forms (cyclic monomer, parallel and anti-parallel dimer) by NMR analysis. MALDI-ToF mass spectrometry allows discriminating between monomer and dimers only.

The purity of compounds of the invention can be evaluated by RP-HPLC. Briefly, a preparation of compound is submitted to RP-HPLC. The relative purity degree is calculated by integrating the peak surfaces. It is expressed as the compound peak surface/surfaces of the whole peaks. It is usual to prepare compounds of the invention that each exhibits a purity degree of at least 95 %, frequently of at least 97 %.

The invention also relates to compositions comprising:
A SAEP III peptide, wherein the peptide is essentially in dimeric parallel form;
A SAEP II peptide, wherein the peptide is essentially in dimeric anti-parallel form; or
mixtures thereof.

By "essentially" it is meant that in the compositions, a particular form is at least 95 %, preferably at least 97%, more preferably 98% pure.

Mixed compositions in which the SAEP II peptide is present under several forms (dimeric parallel, dimeric anti-parallel and/or monomeric forms) may spontaneous result from the evolution of a composition comprising a single entity, e.g. the dimeric parallel form, kept at an appropriate temperature over a certain period of time. This may be revealed by e.g. RP-HPLC analysis. The respective amounts of the various peptide forms may be quantified by the same token.

The SAEP II dimers are useful as such as a detoxifying agent of Gram-negative bacterial LPS in vitro as well as in vivo. Accordingly, they may be used to prevent or treat pathological conditions due to the release of LPS into the systemic circulation, e.g. into blood, as a result of Gram-negative bacteria infections. These conditions include i.a. endotoxicosis, bacterial sepsis and septic shock.

Therefore, the invention encompasses:
The pharmaceutical use of a compound or composition of the invention;

A pharmaceutical composition comprising a compound or a composition of the invention together with a pharmaceutically acceptable diluent or carrier;
The use of a compound or composition of the invention in the preparation of a medicament for treating or preventing septic shock; and
A method for treating or preventing septic shock, which comprises administering a therapeutically or prophylactically effective amount of a compound or composition of the invention, to an individual in need.

A compound or composition of the invention may be administered to mammals, i.e. humans, when a Gram-negative bacteria infection is diagnosed that may lead to endotoxicosis, bacterial sepsis and/or septic shock. Gram-negative bacteria that may be responsible for these fatal disorders include i.a., *N. meningitidis*, *E. coli*, *Salmonella typhi*, *Bordetella pertussis* and *Pseudomonas aeruginosa*. A compound or composition of the invention may be administered to an individual in need by a systemic route, preferably the intravenous route. The dose to be administered depends on various factors including i.a. the age, weight, physiological condition of the patient as well as the infection status. It may be administered once or several times until the risk of fatal event is avoided.

Since the SAEP II dimers and the SAEP2-L2 peptide are also able to detoxify LPS in vitro, the invention also relates to a LPS-peptide complex comprising (i) a LPS moiety of Gram-negative bacteria, and (ii) a SAEP II peptide dimer or the SAEP2-L2 peptide; wherein the LPS moiety and the SAEP II peptide dimer or the SAEP2-L2 peptide are non-covalently bound to each other.

LPS detoxification may be assessed in a number of assays referred to in the European Pharmacopeia They include the Limulus Amebocyte Lysate (LAL) assay; the pyrogen test in rabbits and the acute toxicity assay in D-galactosamine sensitized mice. These assays are illustrated hereinafter in the examples. In each of the assays the effect of LPS and that of the LPS-peptide complex are measured in parallel so that a detoxification ratio be established.

In the LAL assay, the detoxification ratio is expressed by the LPS/LPS-peptide complex ratio. In the pyrogen test and the acute toxicity assay, the detoxification ratio is expressed by the LPS-peptide complex/LPS ratio.

Significant detoxification is achieved, when the detoxification ratio measured in:
(i) the LAL assay is at least of 100, preferably 500, more preferably 1000;
(ii) the pyrogen test is at least of 50, preferably of 100, more preferably 500; or
(iii) D-galactosamine mice is at least of 50, preferably of 100, more preferably of 200.

Detoxification may also be evaluated while comparing the effect of LPS and a LPS-peptide complex on the release of pro-inflammatory cytokines such as IL6, IL8 and TNFα, in in vitro or in vivo assays. These assays are illustrated hereinafter in the examples. Significant detoxification is achieved, when the LPS-peptide complex allows for at least 25-fold decrease, preferably at least 50-fold, more preferably at least 75-fold, most preferably at least 100-fold decrease in IL6 secretion in the in vivo assay as described in the examples, section 5.4.1.

LPS-peptide complex of the invention is advantageously characterized by a molar LPS: peptide ratio of from 1:1.5 to 1:0.5, preferably 1:1.2 to 1:0.8, more preferably of 1:1.1 to 1:0.9, most preferably 1:1.

For use in the complex of the invention the LPS is advantageously a LPS of *N. meningitidis*; *E. coli*; *Salmonella typhi*; *Salmonella paratyphi*; *Shigella flexneri*; *Haemophilus influ-* enzae; Helicobacter pylori; Chlamydia trachbmatis; Bordetella pertussis; Brucella; Legionella pneumophia; Vibrio cholera; Moraxella catharralis; Pseudomonas aeruginosa; Yersinia; and Kiebsiella pneumonia.

As mentioned in the introduction, detoxified LPS may be useful as vaccinal agent against Gram-negative bacteria infection.

Meningitis is a life-threatening disease of either viral or bacterial origin. H. influenzae and N. meningitidis are respectively responsible for about 40 and 50 % of bacterial meningitis. While a vaccine against H. influenzae has been on the market for more than 10 years, there is still a need for a vaccine against N. meningitidis.

Meningococcal invasive diseases may manifest as either an inflammation of the meninges of the brain and spinal cord (meningitis) or a systemic infection of the blood (meningococcal sepsis or meningoccaemia).

Meningococci are classified using serological methods based on the structure of the polysaccharide capsule. Thirteen antigenically and chemically distinct polysaccharides capsules have been described. Almost all the invasive meningococcal diseases are caused by five serogroups: A, B, C, Y and W-135. The relative importance of each serogroup depends on the geographic location. Serogroup B is responsible for the majority of meningococcal diseases in temperate countries.

While conjugated polysaccharide vaccines already exist against serogroup A, C, Y and W-135, there is currently no vaccine available against the serogroup that is prevalent in the USA and Europe. Indeed, the use of capsular polysaccharide as a vaccinal agent for preventing menB diseases has been problematic.

Therefore, the use of N. meningitidis LPS as vaccinal agent, in a fully antigenic and ad hoc detoxified form, is a promising alternative that may offer a desirable vaccinal coverage, in particular to serogroup B.

As mentioned hereinabove in the introduction, the major constituent of the cell wall of Gram-negative, non-enteric bacteria such as Neisserias, Bordetellas, Haemophilus and Moraxellas, is a lipooligosaccharide (LOS) rather than a true LPS. Nevertheless, for the purpose of this application, the term LPS shall be understood as encompassing LOS. LOSs constitute a particular sub-class of LPS. The terms "meningococcal LPS" and "meningococcal LOS" are used hereinafter interchangeably.

FIG. 1 shows a scheme of the structure of a N. meningitidis LOS. LOS is constituted by a branched oligosaccharide composed of 5 to 10 monosaccharides linked to lipid A by a KDO. Lipid A and the inner core constituted by two KDO, two heptoses (Hep I and II) and a N-acetylated glucosamine (GlcNAc), are conserved intraspecies. The remaining of the oligosaccharide chains that constitutes the outer core (α-chain attached to HepI; β-chain attached to position 3 of HepII; and γ-chain attached to position 2 of HepII) is variable according to the immunotypes (ITs). N. meningitidis LPS can be classified into 13 immunotypes, based on their reactivity with a series of monoclonal antibodies (Achtman et al, 1992, J Infect. Dis. 165: 53-68). Differences between immunotypes come from variation in the composition and conformation of the oligosaccharides chains. This is to be seen in the table hereinafter.

| IT | α-chain | β-chain | Additional HepII substituents in position 6 or 7 | γ-chain |
|---|---|---|---|---|
| L1 | NeuNAcα2-6Galα1-4Galβ1-4Glcβ1-4 | PEA (1-3) | None | GlcNAcα1-2 |
| L2 | NeuNAcα2-3Galβ1-4GlcNAcβ1-3Galβ1-4 Glcβ1-4 | Glcα (1-3) | PEA (1-6) ou PEA (1-7) | $(Ac_{0.4})$-GlcNAcα1-2 |
| L3 | NeuNAcα2-3Galβ1-4GlcNAcβ1-3Galβ1-4 Glcβ1-4 | PEA (1-3) | None | GlcNAcα1-2 |
| L4 | NeuNAcα2-3Galβ1-4GlcNAcβ1-3Galβ1-4 Glcβ1-4 | H (3) | PEA (1-6) | $Ac_{0.5}$-GlcNAcα1-2 |
| L5 | NeuNAcα2-3Galβ1-4GlcNAcβ1-3Galβ1-4Glcβ1-4Glcβ1-4 | Glcα (1-3) | None | $(Ac_{0.6-0.4})$-GlcNAcα1-2 |
| L6 | GlcNAcβ1-3Galβ1-4 Glcβ1-4 | H (3) | PEA (1-6) ou PEA (1-7) | GlcNAcα1-2 |
| L7 | NeuNAcα2-3Galβ1-4GlcNAcβ1-3Galβ1-4 Glcβ1-4 | PEA (1-3) | None | GlcNAcα1-2 |
| L8 | Galβ1-4 Glcβ1-4 | PEA (1-3) | None | GlcNAcα1-2 |
| L9 | Galβ1-4GlcNAcβ1-3Galβ1-4 Glcβ1-4 | PEA (n.e.) | n.e. | GlcNAcα1-2 |
| L10 | Galβ1-4GlcNAcβ1-3Galβ1-4 Glcβ1-4 | PEA (n.e.) | n.e. | (n.e.)-GlcNAcα1-2 |
| L11 | Galα1-4Galβ1-4Glcβ1-4 | PEA (n.e.) | n.e. | (n.e.)-GlcNAcα1-2 |
| L12 | n.e. | PEA (n.e.) | n.e. | (n.e.)-GlcNAcα1-2 |
| L13 | n.e. | n.e. | n.e. | n.e. |

As indicated in the above table, a phospho ethanol amine (PEA) replaces the Glc of the β-chain at position 3 of HepII in LOS L1, L3, L7 and L8. A PEA is attached in position 6 or 7 in LOS L2, L4 and L6. LOS L2, L3, L4, L5, L5, L7 may also be sialylate with N-acetyl neuraminidic acid, on the terminal galactose (Gal) of the α-chain.

Immunotypes L1-L8 are essentially associated with serogroups B and C, while immuno-types L9-L12 are found predominantly within serogroup A.

While any LOS can be equally detoxified, it may be advantageous to employ LOS L8 in the complexes of the invention as these latter are further intended to vaccinal use. Indeed, the complete structure of the LOS L8 α-chain is common to all the immunotypes for which the structure has been identified so far Kahler & Stephens, 1988, Crit. Rev. Microbiol. 24: 281).

Meningococcal strains frequently express several immunotypes, the presence of which may be influenced by the culture conditions. If there is a special interest in LOS L8, it may be desirable to extract this LOS from a strain known to predominantly express the L8 immunotype, or even better, to exclusively express it. Strain A1 (also called 2E) of serogroup A, strain M978 of serogroup B (Mandrell & Zollinger, 1977, Infect. Immun. 16: 471; Gu et al, 1992, J. Clin. Microbiol. 30: 2047-2053; Zhu et al, 2001, FEMS Microbiol. Lett. 203: 173), strain 8680 of serogroup B (Dominique Caugeant collection) and strain 8532 (U.S. Pat. No. 6,476,201) are suitable to this end. These strains are obtainable from the scientific community (U.S. Pat. No. 6,531,131).

Monoclonals that are specific for LOS L8 include Mab 2-1-18 (Moran et al, 1994 Infect Immun. 62: 5290-5295; Mandrell et al, 1986, Infect Immun. 54: 63-69) Mab 6E7-10 (Braun et al, 2004, Vaccine 22: 898-908) Mab 4387A5 and 4385G7 (Andersen et al, 1995, Microb. Pathog. 19: 159-168; Gu et al (supra)).

For use in the complexes of the invention, LPS may be obtained by conventional means; in particular it may be extracted from a Gram-negative bacterial culture and then purified according to classical procedures. Numerous descriptions of such procedures may be found in the literature. This includes i.a. Gu & Tsaï, 1993, Infect. Immun. 61 (5): 1873, Wu et al, 1987, Anal. Biochem.160: 281 and U.S. Pat. No. 6,531,131 all cited by way of illustration only. An LPS preparation may also be quantified according to procedures well-known in the art. A convenient method is the KDO dosage with high performance anion exchange chromatography (HPAEC) PAD.

LPS may be complexed to the compounds of the invention as such or in a conjugated form. LPS conjugates can be conventionally prepared by covalently linking LPS to a carrier molecules, e.g. a polypeptide or a peptide; either through a direct covalent link or using chemical spacer/linker molecules. Examples of carrier molecules include the pertussis, diphtheria or tetanus toxoid and outer membrane proteins (OMP) such as the OMP1 or OMP2/3 of N. meningitidis. Numerous descriptions of such conjugation processes may be found in the literature. U.S. Pat. No. 6,531,131 is cited by way of illustration only.

When used in a conjugate form, the LPS is advantageously conjugated before being complexed to the compounds of the invention. This being said, non-conjugated LPS is suitable as well.

The invention also relates to:

A process for detoxifying Gram-negative bacteria LPS, which comprises mixing together (i) a LPS of Gram-negative bacteria and (ii) a compound of the invention; and A process for preparing a LPS-peptide complex, which comprises mixing together (i) a LPS of Gram-negative bacteria and (ii) a compound of the invention.

For use in the processes of the invention, both constituents are advantageously in a liquid medium, suitably water. LPS and compound solutions are advantageously sterilized before mixing. The preparation process is advantageously achieved under sterile conditions. Upon mixing, a precipitate containing the complex is formed. It can be recovered i.a. by centrifigation, and submitted to one or several washing steps, if necessary.

As mentioned above, LPS-peptides complexes of the invention are useful in that they can be safely administered to mammals. Indeed, LPS is detoxified to such an extent that adverse events shall not occur upon administration. As a matter of example, a LPS-peptide complex that exhibits a pyrogenic threshold superior to 1, preferably 10 ng/mL/kg IV dose in the rabbit pyrogen assay, is suitable. Alternatively or additionally, one may refer to the LAL assay. As vaccines containing LPS amounting 3,000 -5,000 LAL endotoxin units have already been authorized for human administration (Frederiksen et al, 1991, NIPH Annals 14 (2): 67), it is possible to predict that a dose of the vaccine of the invention may safely exhibit 5,000 LAL endotoxin units or less, e.g. less than 3,000, 2,000, 1,000 or 500 LAL endotoxin units.

As a matter of example, a complex that exhibits e.g. 100 endotoxin units (EU)/μg in the LAL assay, may be therefore acceptable for administration at a dose of 20 μg. This is achievable with the complexes of the invention as they may exhibit an LAL activity inferior to 50 EU/μg, frequently inferior to 20 EU/μg.

Further, LPS-peptides complexes of the invention are stable, even in physiological conditions. By "stable" it is meant that the detoxification status of LPS in the complexes remains constant over time, at least 3, 6, 12 or 18 months. This can be monitored by evaluating the detoxification ratio at intervals, i.e. in at least one of the assays listed above. No significant difference is observed in the detoxification ratio over time.

LPS-peptides complexes of the invention are also useful in that they are able to induce an immune response against Gram-negative bacteria. This may be shown upon administration of complexes to mammals, e.g. rabbits, mice or humans, followed by ELISA analysis of the sera to reveal the presence of antibodies (i.a. immmunoglobulins G or M) specific for LPS. Advantageously, the immune response (antibodies induced) may have bactericidal and/or opsonic activity.

The ability of the immune response induced by the complexes of the invention to protect against Gram-negative bacteria infection may be evaluated in appropriate animal models that are currently specific for a bacterial species or disease. It is within the skills of the professionals in the art of vaccines to select a known animal model with regard to a particular bacteria or disease.

As a matter of example, the ability of the immune response induced by the complexes of the invention to protect against N. meningitidis may be evaluated in the mouse intraperitoneal infection model (Schryvers et al, 1989, Infect. Immun. 57 (8): 2425 and Danve et al, 1993, Vaccine 11 (12): 1214). It may be also evaluated in humans by measuring the bactericidal activity of the human serum after a complex is administered. Indeed, this test has been proposed to serve as a surrogate test of protection at least for N. meningitidis serogroup B (Holst et al, 2003, Vaccine, 21: 734). A human serum bactericidal activity (SBA) titer superior or equal to 4 has been shown to correlate with protection.

In view of this, the invention also relates to:

(i) The use of a LPS-peptide complex of the invention, for treating or preventing a Gram-negative bacterial infection;

(ii) A pharmaceutical (vaccinal) composition comprising a LPS-peptide complex of the invention and a pharmaceutically acceptable diluent or carrier;

(iii) The use of a LPS-peptide complex of the invention, in the preparation of a medicament for treating or preventing a Gram-negative bacterial infection;

(iv) A method for inducing an immune response in a mammal against a Gram-negative bacteria LPS or a Gram-negative bacteria, which comprises administering an effective amount of a LPS-peptide complex of the invention, to the mammal; and (v) A method for treating or preventing a Gram-negative bacterial infection, which comprises administering a therapeutically effective amount of a LPS-peptide complex of the invention, to an individual in need.

A vaccinal composition of the invention can be administered by any conventional route, in particular by systemic or intramuscular route; as a single dose or as a dose repeated once or several times, e.g. two or three times at intervals, e.g. at 1, 2, 3, 6, 10, 12 month-interval. A vaccinal composition of the invention can be conventionally formulated, advantageously in liquid form. If necessary, an adjuvant can be added to the vaccinal composition of the invention; however, it is indicated that complexes of the invention can be sufficiently immunogenic so that the presence of adjuvant in the vaccinal compositions is not required.

The appropriate dosage depends on various parameters, for example the individual treated (adult or child), the mode and frequency of administration and the LPS detoxification status, as can be determined by persons skilled in the art. In general, it is indicated that a dose for administration to a human adult should not excess 10,000; advantageously 8,000; preferably 5,000; more preferably 1,000; most preferably 500 LAL Endotoxin Unit. In the LAL assay, the value measured for a complex of the invention may commonly be as low as 10-20 EU/μg. Therefore, a dose can contain from 1 to 500, advantageously from 2.5 to 100, preferably from 10 to 50, more preferably from 15 to 30 μg.

It is reminded that, by convention, amounts of complex are always expressed as LPS content. Accordingly and by way of example only, "50 μg of complex" actually means 50 μg of LPS in the complex preparation.

The Examples reported hereinafter further illustrate the invention by reference to the following figures.

BRIEF DESCRIPTION OF THE DRAWINGS

FIG. 1A shows the structure of the LPS L8 of *N. meningitidis*. Kdo stands for 2-keto, 3-desoxy octulosonic acid; Hep stands for heptose; Glc stands for glucose; Gal stands for galactose; and GlcNAc stands for N-acetylated glucosamine.

FIG. 1B shows the reaction that occurs upon LPS treatment with acetic acid.

FIGS. 5A-5C show an enlargement of the region of the $^1$H NMR spectra of FIGS. 4A-4C comprised between 6.5 and 7.5 ppm.

EXAMPLE 1

Figure 2A:
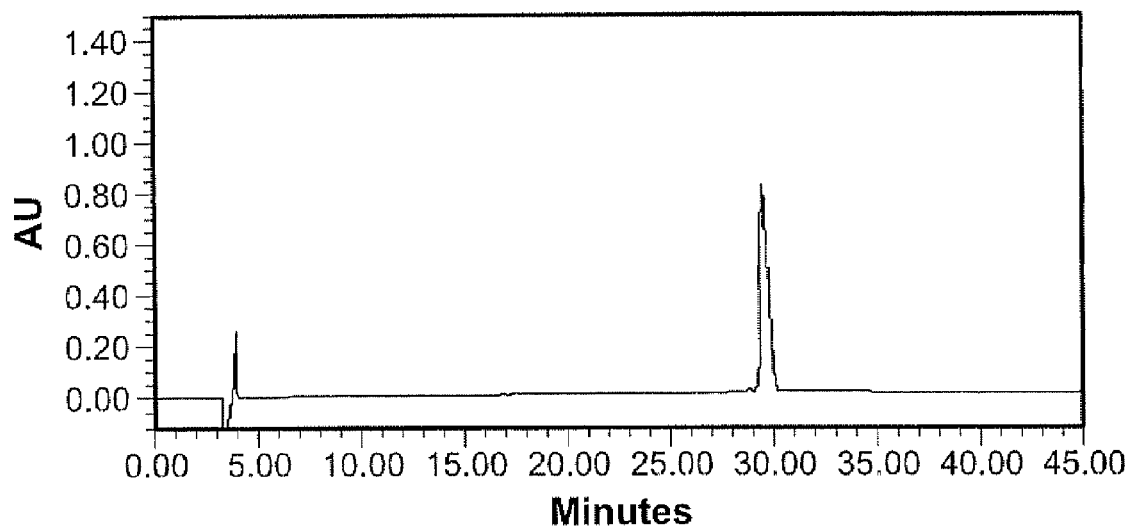
FIGS. 2A-2C show the HPLC chromatogram obtained at 214 nm with a composition essentially comprising the SAEP2-L2 peptide in monomeric form (2A), in parallel dimeric form (2B) and anti-parallel dimeric form (2C). Coordinates are: times (min) and absorbance unit (AU).

Preparation of the SAEP2-L2 Parallel Dimer 1.1. Synthesis

The synthesis of the corresponding linear monomer is achieved on solid phase using a computer-driven automatic synthesizer Milligen 9050 (Millipore Inc.) operating with columns containing resin supports e.g. polyoxyethylene glycol-activated polystyrene, or activated polyacrylamide, which are appropriately activated according to the choice of the first amino acid of the selected peptide sequence as reported by Atheron & Shepard: in Solid phase peptide synthesis, 1989, IRL press, Oxford U.

The synthesis cycle proceeds step-by-step, according to the reported linear sequence. It is performed in pure solvent dimethylformamide (DMF). Side-protected, activated amino acids are used.

The thiol group of the Cys residue in position 10 (Cys-10) is protected with the acid-labile group Trityl (triphenyl-methyl derivative, Trt). The thiol group of the Cys residue in position 4 (Cys-10) is protected with the acid-resistant group S-acetamido-methyl (Acm).

All the amino acids are activated at the —COOH side by O-penta-fluorophenyl-phosphate esters (O-Pfp-derivatives). They are temporarily protected at the -NH$_2$ side by 9-fluorenyl-methyloxy-carbonyl esters (Fmoc-derivatives).

Once synthesized, the protected peptide is cleaved from the resin support using TFA 95% in the presence of the scavenger ethanditiol at 2-5% (v/v). In these conditions, the thiol group of the Cys-10 is de-protected, while the thiol group of the Cys-4 remains Acm-protected. The free, Acm-protected peptide is concentrated by vacuum-evaporation and then recovered by precipitation with ether at 80% (v/v) final concentration.

The Cys-4 protected, Cys-10 de-protected peptide is dried under vacuum, then solubilized in water at the concentration of 1 to 10 mg/mL and adjusted at pH 7.50 with 0.1 M aqueous ammonia. In order to achieve dimerization through the Cys 10 residues, oxidation is then performed by vigorous string of the aqueous solution at 4° C., under a pressure of 1 Atm, for 18-24 hours. Complete oxidation of the thiol groups is determined by the Elman calorimetric assay.

The partly oxidized peptide in solution at the concentration of 1 to 10 mg/mL is then processed for de-protection of the remaining Cys-4 S-Acm functions. To this end, the peptide solution is added with mercuric acetate at a final concentration of 0.1 M, using phenol at 2-5% (v/v) as scavenger. The solution is again vigorously stirred at 20° C., under a pressure of 1 Atm, for 18-24 hours. Complete oxidation of the thiol groups is determined by the Elman calorimetric assay.

1.2. Purification

In order to remove the low-MW molecules contained in the peptide preparation (scavenger, mercuric acetate etc.), this latter is applied on a reverse-phase column Sep-Pack (Millipore) operated under pressure of 1 Atm. In an aqueous solvent, the peptide is retained on the column by hydrophobic forces, while all the hydro-soluble, low-MW molecules go with the flow-through. The peptide is then eluted by a mixture of methanol-water 50-70% (v/v). The peptide eluted in the alcoholic solvent, is recovered by vacuum concentration and solubilized again in water at the desired concentration.

Final purification is achieved on HPLC-operated reverse-phase C18 column (dimensions=250×4 mm) using a linear gradient 0-100% of Solvent A (0.1% TFA (trifluoroacetic acid) in water) and Solvent B (nitryl acetate 80% in water). In these conditions, the parallel dimer elutes as a single sharp peak. Peak fractions are recovered.

The preparation is kept in lyophilized form, at +2-+6° C., under a neutral gas, argon or nitrogen.

1.3. Characterization of the Purified Peptide 1.3.1. Amino Acid Composition

The amino acid composition is analysed by the Pico-Tag method (Millipore). Results are reported in the table hereinafter.

| Amino acid | Theoretical (moles/mole) | Found (moles/mole) |
|---|---|---|
| Lysine | 6.0 | 5.90 |
| Threonine | 2.0 | 2.00 |
| Phenylalanine | 2.0 | 2.05 |
| Leucine | 6.0 | 6.10 |
| Cysteine | 4.0 | 3.85 |

1.3.2. Molecular Mass

The molecular mass is measured by Ion Cyclotron Resonance (ICR). The value found is 2,387.33±0.3 AMU, a value coherent with the elementary structure $C_{110}H_{190}O_{24}N_{26}S_4$ of the peptide formula.

EXAMPLE 2

Preparation of the SAEP2-L2 Monomer and Anti Parallel Dimer 2.1. Synthesis

The synthesis of the linear monomer is performed as in Example 1, except that a the different methodology is used for protecting the thiol groups of the cysteine residues: Both Cys-4 and -10 are protected at their —SH group by the acid-labile group Trityl (triphenyl-methyl, Trt).

The protected peptide is cleaved from the resin support by TFA 95%, in the presence of the scavenger Ethandithiol at 2-5% (v/v). In these conditions, the thiol groups of both Cys-4 and 10 residues are de-protected. The cleaved and de-protected peptide is then concentrated under vacuum-evaporation and recovered by precipitation with ether 80% (v/v).

The de-protected peptide is solubilized in water at the concentration 1 to 10 mg/mL and the pH is adjusted to 7.50 with 0.1 M aqueous ammonia.

Oxidation is then performed by vigorous string of the aqueous solution for 18-24 hours, at 4° C., under pressure of 1 Atm. Complete oxidation of the thiol groups is determined by the Elman calorimetric assay.

2.2. Purification of the Peptides

The peptides in solution actually constitute a mixture of cyclic monomer (about 40%) and anti-parallel dimer (about 60%). Each form is purified by preparative Reverse-phase HPLC chromatography. Indeed, it is possible to separate the cyclic monomer from the anti-parallel dimer since these forms elute, each as a single sharp peak, at different retention times. The anti-parallel dimer elutes at a lower retention time. This is consistent with the different molecular symmetry of the two dimers. The anti-parallel peptide may assume a lower minimal energy in aqueous solvents by virtue of its lower internal steric hindrance of the side-chains, similarly to the "trans" vs "cis" conformation of any other isomeric entities.

All preparations are kept in lyophilized form, at +2-+6° C., under a neutral gas, argon or nitrogen.

2.3. Characterization of the Antiparallel Dimer 2.3.1. Amino Acid Composition

The amino acid composition is analysed by the Pico-Tag method (Millipore). Results are reported in the table hereinafter.

| Amino acid | Theoretical (moles/mole) | Found (moles/mole) |
|---|---|---|
| Lysine | 6.0 | 6.10 |
| Threonine | 2.0 | 1.95 |
| Phenylalanine | 2.0 | 1.90 |
| Leucine | 6.0 | 6.05 |
| Cysteine | 4.0 | 3.90 |

2.3.2. Molecular Mass

The molecular mass is measured by Ion Cyclotron Resonance (ICR). The value found is 2,387.30±0.3 AMU, a value coherent with the elementary structure $C_{110}H_{190}O_{24}N_{26}S_4$ of the peptide formula.

EXAMPLE 3

Further Characterization of the Monomer, Parallel and Antiparallel Dimers By HPLC-reverse Phase, NMR and MALDI-ToF Mass Spectrometry The dimeric parallel peptide as prepared in Example 1 and the monomeric and dimeric antiparallel peptides as prepared in Example 2 are characterized by HPLC-reverse phase (FIGS. 2A-2C) and NMR (FIGS. 4A-4C and 5A-5C).

3.1. Characterization By HPLC-reverse Phase

Experimental Conditions

This technique is carried out on a IPLC chain (Waters™), using the Millenium software 32 V30501 (Waters™) for data acquisition. The analytical column Macherey Nagel™ ref 720014.6 (Nucleosil 5 µm C18 100Angstrom 250×4.6 mm) is operated at 25° C. 30-40 µg of each lyophilised peptide are diluted first in 30 µl water; to which is added 30 µl of trifluoroacetic acid (TFA) 0.1% in water.

A mixture of the monomeric, dimeric parallel and antiparallel peptides is also prepared by mixing 40 µg of a powdered preparation of each peptide in 60 µl water; to which is added 60 µl of TFA 0.1% in water.

The column is equilibrated using 20% phase mobile B (TFA 0.1%, $CH_3CN$ 80% in water). Once samples are applied to the equilibrated column, the phase B gradient runs from 20 to 60% within 40 min (1% B/min), at a flow rate of 1 mL/min.

Detection is achieved at 214 nm. Results are to be seen in FIGS. 2A-2C.

Results

Each peptide is eluted at a different retention time. In the experimental conditions described above, elution occurs at the following retention time (RT):

monomer: RT=28.283 min parallel dimer: RT=29.708 min antiparallel dimer: RT=22.059 min The HPLC-RP technique is used to verify the purity of each peptide preparation. The relative purity degree of each peptide is calculated by integrating the peak surfaces. It is expressed as the peptide peak surface/surfaces of the whole peaks.

Figure 2B:
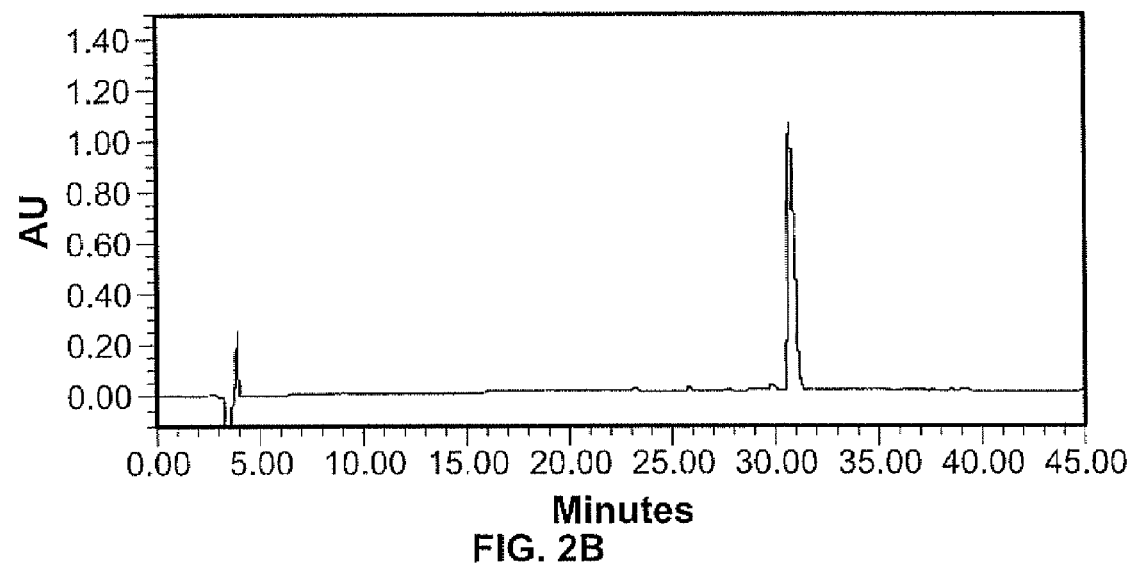
Figure 2C:
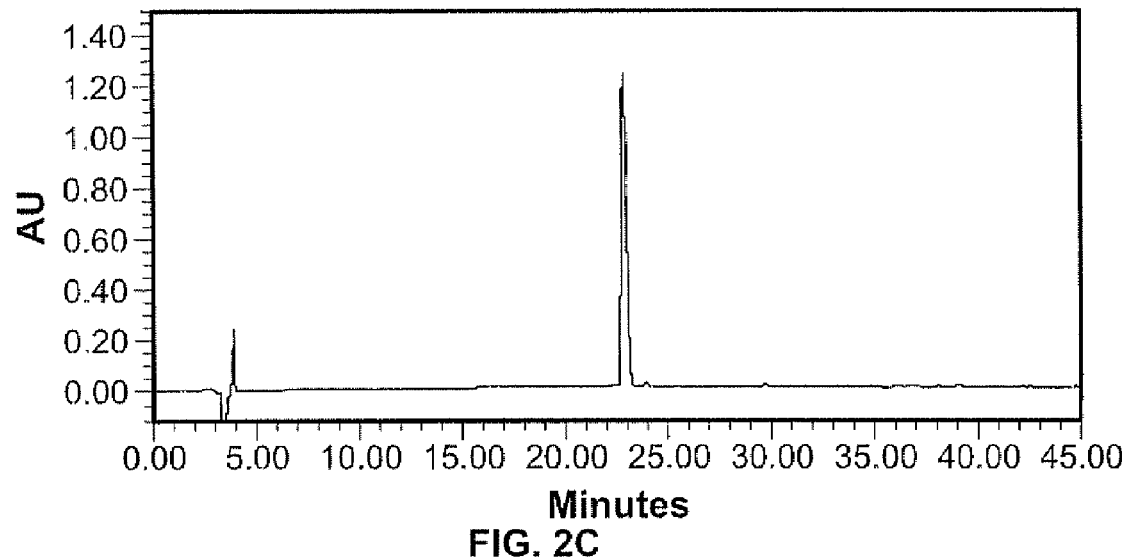

In FIG. 2A-2C, it can be seen that the monomer and parallel and antiparallel dimer preparations exhibit a purity degree of 98, 96.9 and 97% respectively.

Figure 3:
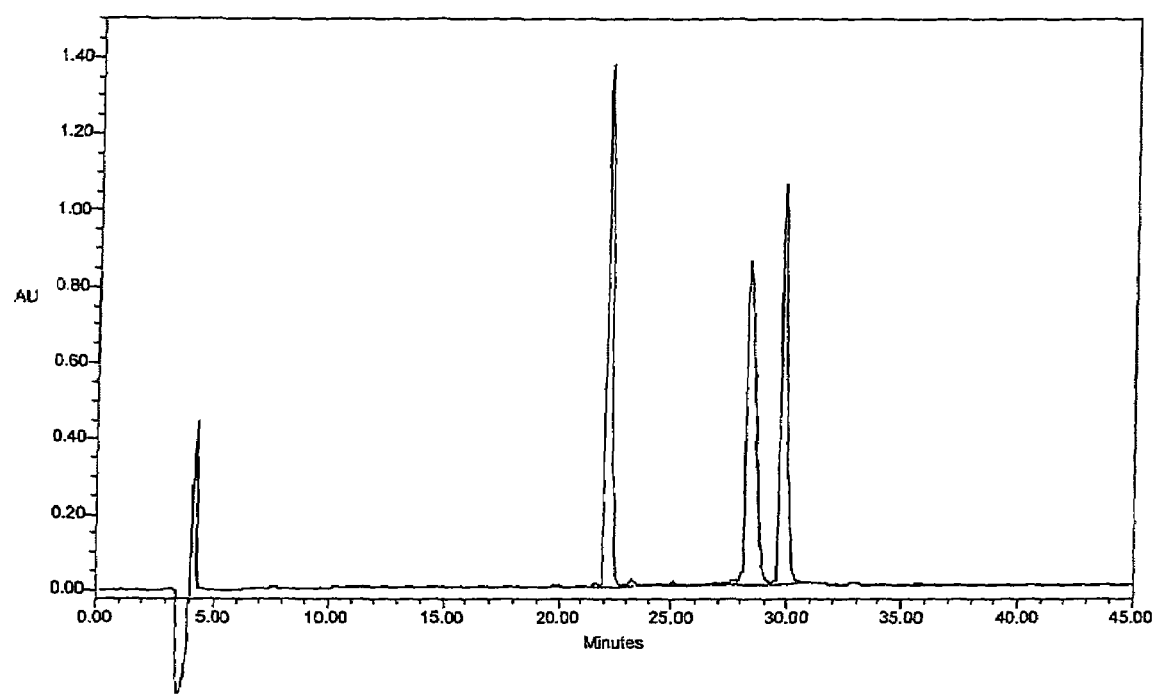
FIG. 3 shows the HPLC chromatogram obtained at 214 nm with a composition comprising the SAEP2-L2 peptide in monomeric form, parallel dimeric form and anti-parallel dimeric form.

FIG. 3 shows the HPLC chromatogram of the mixture.

3.2. Characterization By NMR

Experimental Conditions $^1$H NMR analysis (500 MHz, 25° C., HOD presaturation) is carried out using samples of peptides diluted in a H$_2$O/D$_2$O mixture (90/10 v/v). A Bruker™ DRX500 spectrometer and associated sofware for data acquisition are used.

In more details, peptides preparation kept at −70° C. are used for analysis. Dimeric peptide solutions 0.5 mM are prepared while diluting 1.33 g in 1 mL H$_2$O. 144 µl of the solutions are mixed with 16 µl of D$_2$O 99.9% D in 3 mm NMR tubes. For calibration, an external solution of TSP-d4 (3-(trimethylsilyl)propionic-2,2,3,3, -d4 acid sodium salt; Aldrich ref 29304-0) 0.075% (w/w) in H$_2$O/D$_2$O mixture (90/10 v/v) is used. The spectrometer is calibrated so that the unique resonance signal of TSP-d4 be at 0 ppm.

Results

In the experimental conditions used, $^1$H NMR spectra of the monomer and dimers cover a range from 0 to 9.5 ppm and are composed of 3 main regions:
  from 6.5 to 7.5 ppm;
  from 5.5 to 2.5 ppm; and
  from 2 to 0.3 ppm.

Figure 4A:
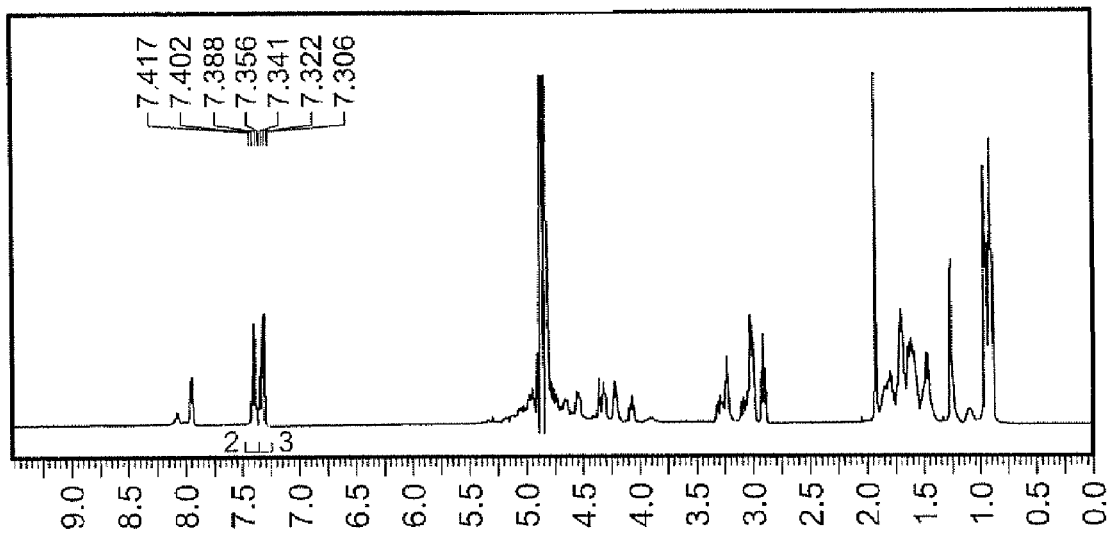
FIGS. 4A-4C show the $^1$H NMR spectra obtained with a composition essentially comprising the SAEP2-L2 peptide in monomeric form (4A), in parallel dimeric form (4B) and anti-parallel dimeric form (3C). In all of them, a peak at 1.9 ppm indicates that the peptide is in an acetate salt form.
Figure 4B:
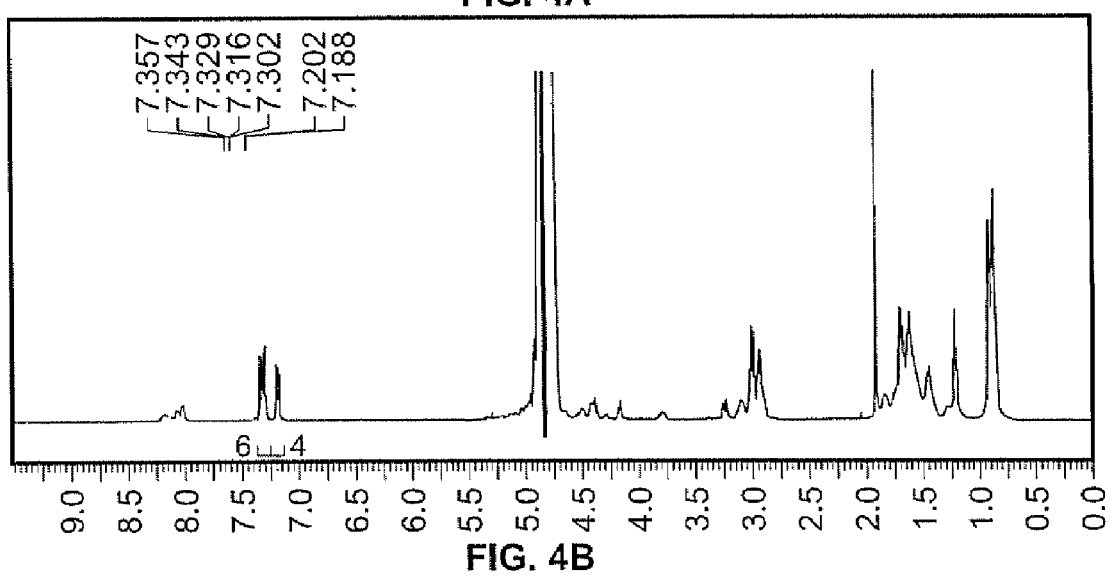
Figure 4C:
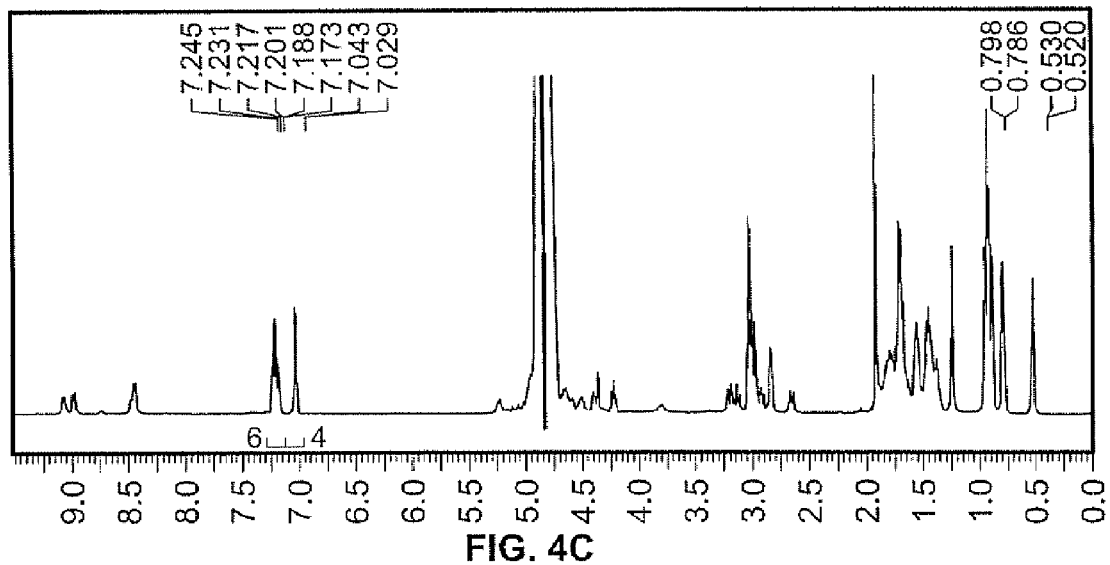
Figure 6:
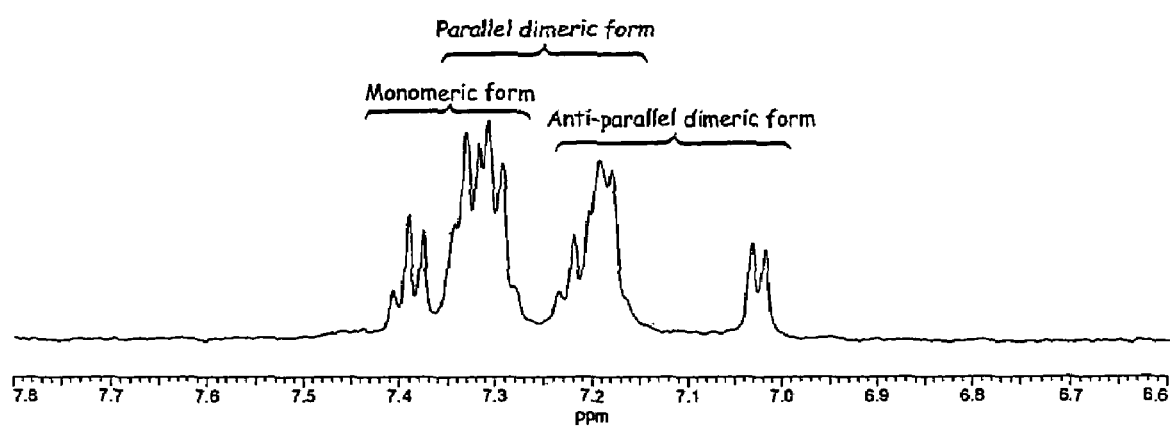
FIG. 6 shows the 6.5-7.5 ppm region of the $^1$H NMR spectrum obtained with a composition comprising the SAEP2-L2 peptide in monomeric form, parallel dimeric form and anti-parallel dimeric form.

This is to be seen in FIG. 4A-4C.

$^1$H NMR spectrum of the monomer is characterized by a NMR pattern of 5 aromatic protons that are expected between 7.25 and 7.45 ppm, in the experimental conditions reported hereinabove. In the experiment reported in FIG. 5A, this NMR pattern is itself composed of a first multiplet from 7.25 to 7.35 ppm with an integral curve corresponding to 3H and a second multiplet (pseudo-triplet), centered at 7.39 ppm with an integral curve of 2H. This latter signal is characteristic of the monomer only.

$^1$H NMR spectrum of the parallel dimer is characterized by a doublet signal between 7.10 and 7.25 ppm corresponding to 4 aromatic protons and a multiplet between 7.25 and 7.40 ppm with an integral curve of 6H. In the experiment reported in FIG. 5B, the 4H doublet is found centered at 7.185 ppm (pics at 7.18 and 7.19 ppm).

$^1$H NMR spectrum of the antiparallel dimer is characterized by a doublet signal 4 aromatic protons between 6.95 and 7.10 ppm and a multiplet between 7.10 and 7.30 ppm with an integral curve of 6H. In the experiment reported in FIG. 5C, the 4H doublet is found centered at 7.025 ppm (pics at 7.02 and 7.03 ppm).

As shown in FIG. 4C, the $^1$H NMR spectrum of the antiparallel dimer is also characterized by two upfield methylic resonances that are expected between (i) 0.40 and 0.65 (doublet) and (ii) 0.70 and 0.85 ppm (doublet). In one experiment, these doublets are found centered at 0.42 and 0.68 ppm. They are observed neither in the monomer, nor in the parallel dimer.

3.3. Identification By MALDI-ToF Mass Spectrometry

Analysis by MALDI-ToF (Mass Assisted Laser Desorption Ionisation —Time of Flight) mass spectrometry allows determining the monoisotopic mass of the peptide. This technique does not discriminate the antiparallel and parallel dimers.

Experimental Conditions

MALDI-ToF analysis is achieved using the Biflex III mass spectrometer (Bruker™) and associated softwares, in a positive reflector mode. Peptides are mixed with a matrix (alpha cyano-4-hydroxy cinnamic acid) that absorbs laser energy.

The spectrometer is externally calibrated with a mixture of synthetic peptides (ACTH 18-39 (adenocorticotropic fragment 18-39) bombesine, and somatostatine 28.

A saturated HCCA matrix solution is prepared while diluting 50 mg HCCA in 300 µl 70% ACN (acetonitril) 0.1% TFA (trifluoroacetic acid) in water.

A ½ saturated HCCA solution is further prepared while diluting vol: vol with 30% ACN, 0.1% TFA in water.

For calibration, primary standard solutions are first prepared in 0.1% TFA. They are as follows:
Adenocorticotropic fragment 18-39 (ACTH 18-39) 100 pmoles/µl (0.247 mg/ML);
Bombesine: 100 pmoles/µl(0.160 mg/mL); and
Somatostatine 28: 100 pmoles/µl (0.31 mg/mL).

A secondary standard solution is prepared as follows:
ACTH 100 pmoles/µl 2 µl
Bombesine 100 pmoles/µl 4 µl
Somatostatine 100 pmoles/µl 4 µl
ACN30%, TFA0.1% 50 µl Peptide solutions at 1 mg/mL in water are diluted down to 0.02 mg/mL with 30% ACN, 0.1% TFA in water.

Calibration and peptide samples are diluted vol: vol with the ½ saturated HCCA solution. Droplets of about 1 µl are deposited on a steel target (Bruker™) and dried by evaporation.

Results

Figure 7A:
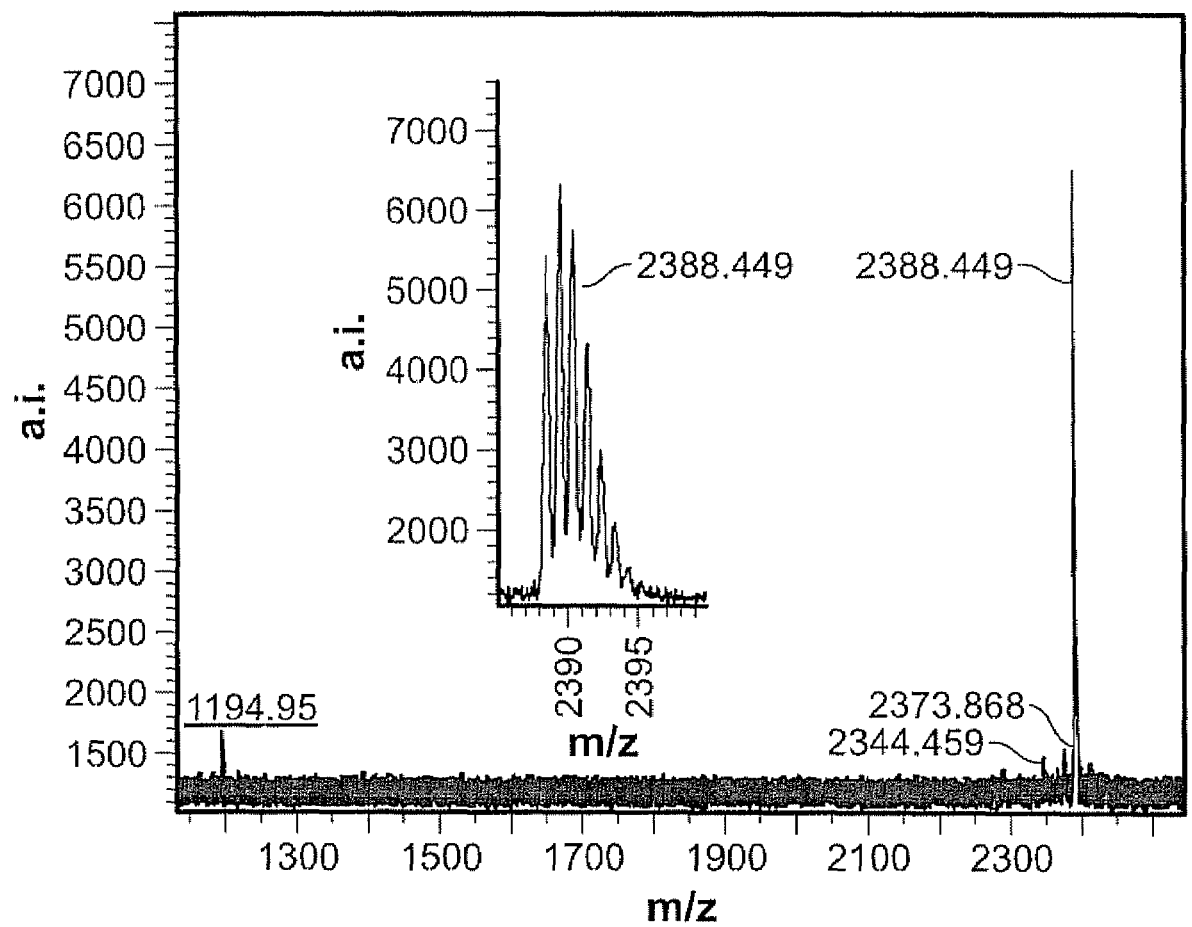
FIGS. 7A-7C show the MALDI-ToF spectra of the calibration standard (7A), the parallel dimer (7B) and the anti-parallel dimer (7C).
Figure 7B:
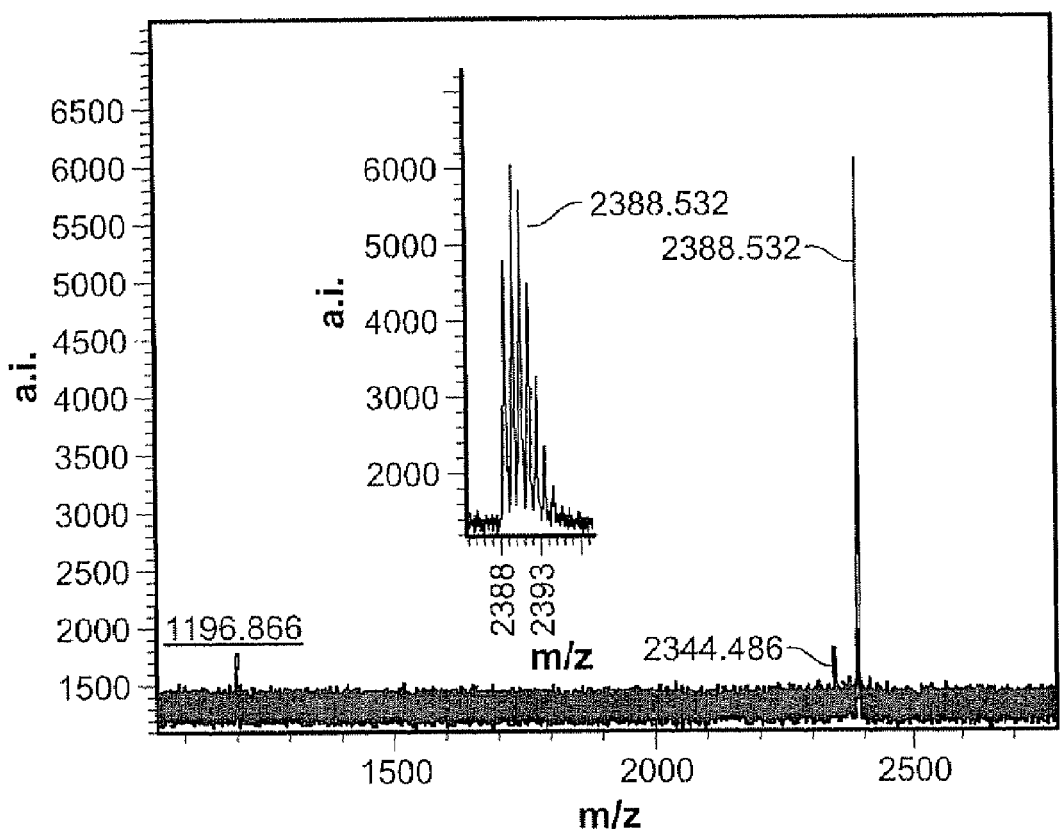
Figure 7C:
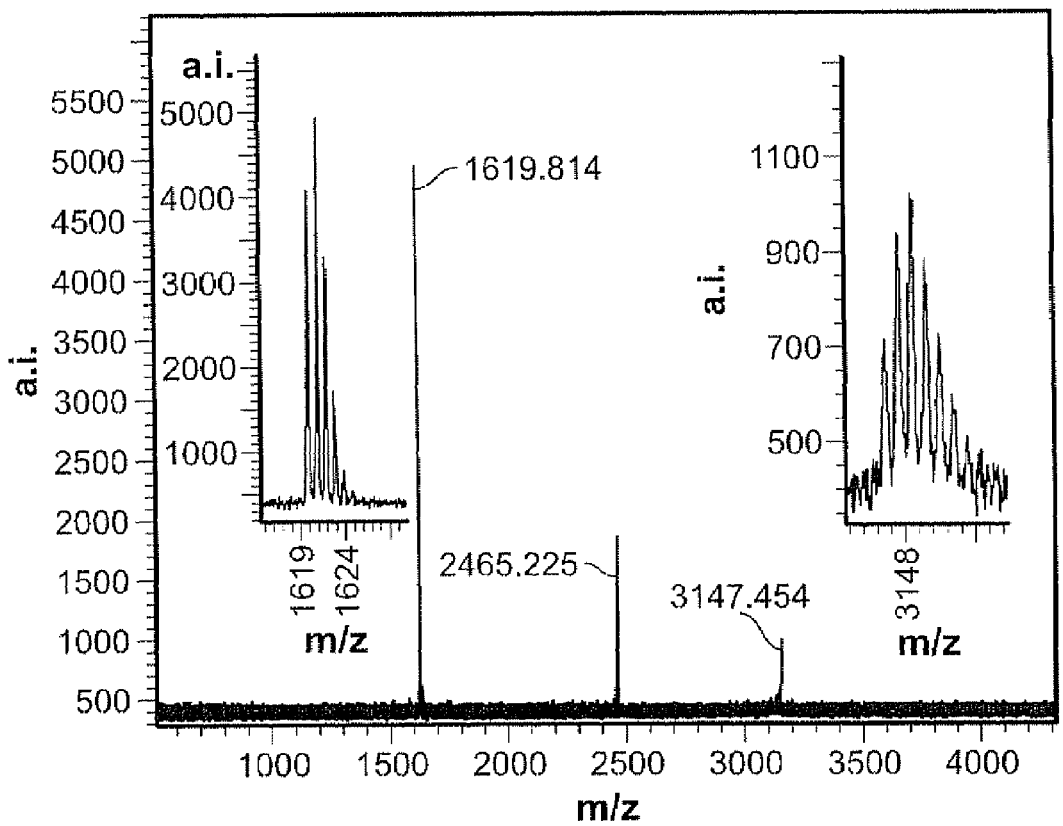

Results are to be seen in FIGS. 7A-7C.

The theoretical monoisotopic masses calculated by the software based on the amino acid sequences are:
ACTH 28 M+H$^+$=2465.199 Da
Bombesine M+H$^+$=1619.823 Da
Somatostatine 28 M+H$^+$=3147.471 Da
SAEP2-L2 M+H$^+$=2388.35 Da.

The standard value used for the control is fixed at ±2 Da compared to the theoretical mass.

As shown in FIG. 7A, the experimental values found for the calibration peptides are 2465.225, 1619.814 and 3147.454 Da respectively. L'ecart de mesure interne est donc (0.026+ 0.009+0.017)/7232.493 =7.2 ppm. (authorized <50 parts per million).

As shown in FIGS. 7B and 7C, the experimental values found for the parallel and antiparallel dimer preparations are 2388.449 and 2388.532 Da. These values are within the identity range (+2 Da) centered on the theoretical values range. This means that the samples contain what is expected.

EXAMPLE 4

Preparation of a LPS L8/peptide I″
Complex/aggregate

4.1. Preparation of LPS L8

4.1.1. Meninge Culture

Preculture: Two mL frozen samples of working seed from a *N. meningitidis* A strain known to express LPS exclusively under the L8 form, are used to inoculate in a 2 1 erlen containing 200 mL of Mueller-Hinton broth (Merck) complemented with 4 mL of a glucose solution in water (500 g/l). This operation is repeated 4 times. Erlens are incubated at 36±1 ° C. for 10+1 hrs while stirring (100 rpm).

Culture: The erlen contents are gathered together and the preculture is complemented with 400 mL of a glucose solution in water (500 g/,) and 800 mL of an amino acid solution. This preparation is used to inoculate the Mueller-Hinton broth, in a 30 l fermentor (B. Braun™) at an initial OD$_{600nm}$ close to 0.05. Fermentation is performed overnight at 36° C., pH 6.8±0.2, 100 rpm, pO$_2$ 30%, and initial flow rate of the air 0.75 l/min/L culture. After 7±1 hrs, (OD$_{600}$ nm, about to 3), the culture is feeded by MH broth at a flow rate of 440 g/h. When the glucose concentration is lower than 5 g/l, the fermentation is stopped. Usually, the final $OD_{600}$ nm is comprised between 20 and 40. Cells are collected by centrifugation for 1 h 30 at 7000 g at 4° C. Pellets are kept frozen at −35° C.

4.1.2. Purification of LPS

First Phenol Extraction

Pellets are defrosted and suspended with 3-volume phenol 4.5% (v/v) and stirred vigorously for 4 hrs minimum at about 5° C.

The bacterial suspension is heated at 65° C. and then mixed v/v with phenol 90% at 65° C. The suspension is stirred vigorously, at 65° C. for 50-70 min and then cooled down to about 20° C.

The suspension is centrifuged for 20 min, at 11 000 g, at about 20° C. The aqueous phase is collected and kept The phenol phase and the interphase are recovered and submitted to a second extraction.

Second Phenol Extraction

The phenol phase and the interphase are heated at 65° C. and mixed with a volume of water equivalent to the volume of the aqueous phase that was previously collected. The mixture is stirred vigorously for 50-70 min at 65° C. and then cooled down to about 20° C. The mixture is centrifuged for 20 min, at 11 000 g, at about 20° C. The aqueous phase is collected and kept The phenol phase and the interphase are recovered and submitted to a third extraction.

Third phenol extraction: Procedure for the second extraction is repeated.

Dialysis

The 3 aqueous phases are dialysed overnight and separately against 40 l of water. The dialysates are pooled together. The dialysate pool is adjusted with Tris 20 mM, $MgCl_2$ 2 mM (one volume per 9 volumes of the dialysate pool). pH is adjusted to 8.0 ±0.2 with NaOH 4 N.

DNAse Treatment

250 UI of DNAse is added per gram of treated bacterial pellet (wet weight). The preparation is stirred at 37±2° C. for 55-65 min. pH is adjusted at 6.8±0.2. The preparation is filtered on 0.22 µm membranes.

Gel filtration: The preparation is purified on a Sephacryl S-300 column (5.0×90 cm; Pharmacia™).

First Alcoholic Precipitation

Powder of $MgCl_2$, $6H_2O$ is added to the LPS-containing fractions pooled together, to reach an $MgCl_2$ concentration of 0.5 M and dissolved while stiring.

While stirring at 5±3° C., dehydrated absolute alcohol is added to a final concentration of 55% (v/v). Stirring is performed overnight at 5±3° C., followed by centrifugation at 5,000 g for 30 min at 5±3° C. The supernatants are discarded and the pellets are submitted to a second extraction.

Second Alcoholic Precipitation

The pellets are resuspended with at least 100 mL $MgCl_2$ 0.5 M, while stiring.

The previous procedure is repeated. Pellets are resuspended with at least 150 mL water.

Final step: Gel filtration is repeated and the LPS-containing fractions pooled together are finally sterilised by filtration (0.8-0.22 µm) and kept at 5+3° C.

As a preliminary control, the LPS preparation is analyzed by SDS-PAGE electrophoresis. Upon silver nitrate staining, a single large band is revealed. This indicates at least that the preparation does not contain any entity other than LPS L8.

The purification process as described allows obtaining about 150 mg LPS L8 per culture liter (yield about 50%).

4.1.3. LPS L8 Quantification: KDO Dosage with HPAEC-PAD

The bibliographic reference for this technique is Kiang et al, (1997) Determination of 2-keto-3-deoxyoctulosonic acid (KDO) with high performance anion exchange chromatography (HPAEC): Survey of stability of KDO and optimal hydrolytic conditions Anal. Biochem. 245: 7.

As shown in FIGS. 1A-1B, LPS comprises in its structure 2 KDO units, one being in a lateral position.

LPS quantification is achieved through dosage of the lateral KDO unit liberated upon soft acid hydrolysis (See FIG. 1B).

Acid Hydrolysis

Samples of the LPS preparation obtained after the last diafiltration of section 4.1.2. are recovered and diluted with water under a final volume of 400 µl in Dionex™ 1.5 mL flasks so that LPS concentration of the samples falls under the etalon range (1.4-72.1 µg/mL).

Samples to be quantified as well as the KDO etalon range are proceeded as follows: 100 µl of the hydrolysis solution (acetic acid 5%; glucuronic acid (GlcA) 20 µg/mL) are added. Hydrolysis is performed for 1 h at 100° C. Flasks are then dried at 40° C. under nitrogen and filled with 400 µl water.

Dosage

This technique is carried out on a HPAEC chain (Dionex™), using the Chromeleon Dionex™ software for data acquisition. The analytical column Carbopac PA1 4×250 mm (Dionex™) is operated at 30° C.

The column is equilibrated with the elution solution (NaOH 75 mM, AcONa 90 mM). 100 µl of sample are injected into the column. Then the column is submitted to an elution flow rate of 1 mL/min for 22 min.

Figure 8:
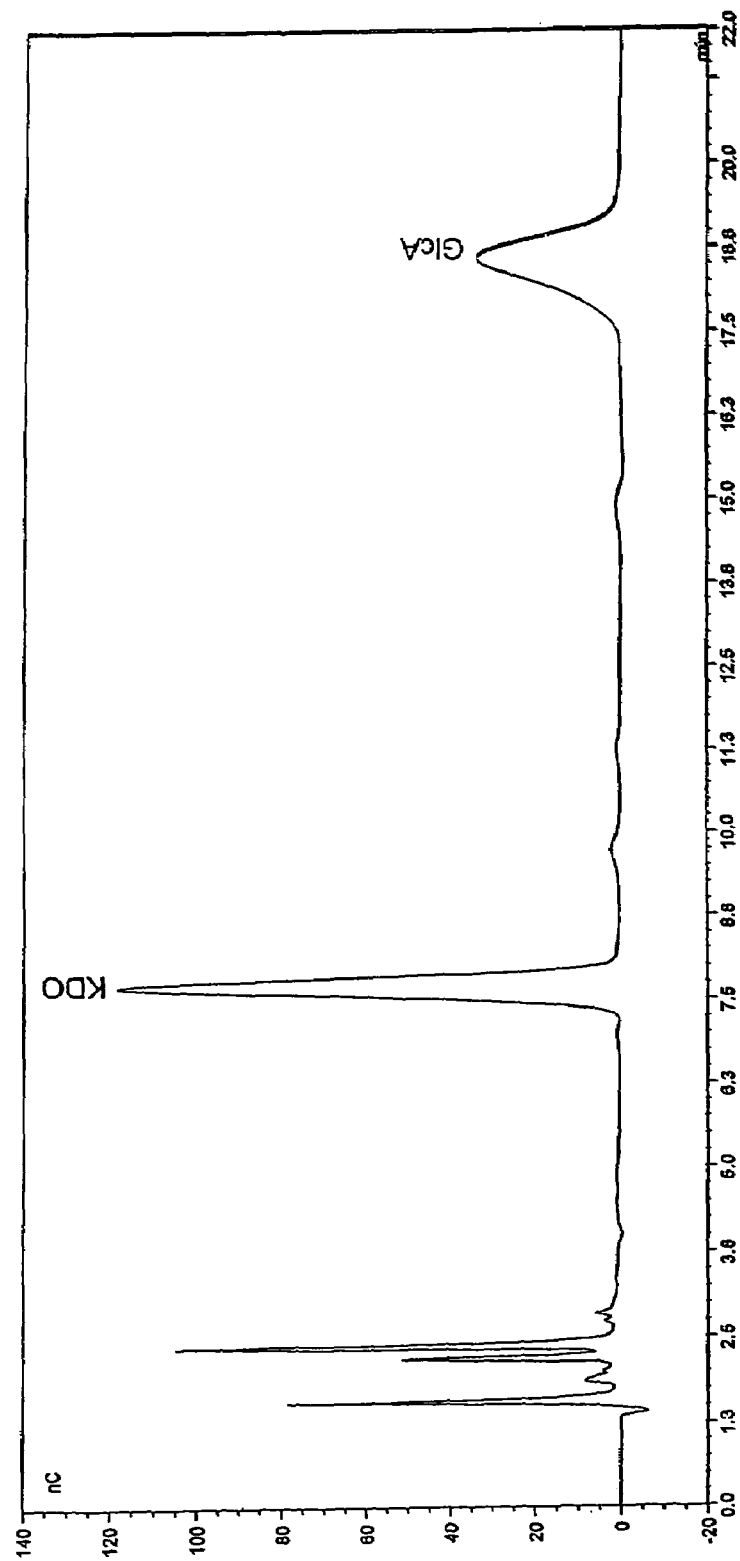
FIG. 8 shows the HPEAC-PAD chromatogram of LPS hydrolysed by acetic acid treatment.

Chromatogram of LPS sample is to be seen in FIG. 8. The KDO amount present in the sample is determined by integration of the KDO peak. As one KDO mole liberated by hydrolysis corresponds to one LPS mole, it is possible to determine the LPS concentration of the initial preparation.

4.2. Preparation of peptides: Peptides are prepared according to the processes described in Examples 1 and 2 above.

4.3. Preparation of the LPS L8/peptide I" Complex/aggregate

Purified LPS is used as pseudo-solution at 1 mg/mL in sterile, pyrogen free water (Milli Q quality, adjusted to pH 7.2 Limulus negative). The translucid pseudo-solution is sterilized by filtration using a 0.22 µm membrane.

A solution of peptide SAEP2-L2 at 1 mg/mL in sterile, pyrogen-free water (Milli Q quality, adjusted to pH 7.2, Limulus negative) is also sterilized by filtration on 0.22 µm membrane.

All the next steps are achieved under sterile conditions.

One volume of the LPS pseudo-solution is added to one volume of the solution of peptide SAEP2-L2. A precipitate (endotoxoid complex) immediately appears. Stirring is carried out for 5 min at room temperature. The preparation is left to stand at +4° C. overnight.

The precipitate (Endotoxoid) is then recovered by centrifugation at 3000 rpm for 10 min. The supernatant is discarded.

The pellet is washed with one volume of sterile, pyrogen free water (Milli Q quality, adjusted to pH 7.2, Limulus negative). Centrifugation/washing steps are repeated five times.

At last, the pellet is resuspended in sterile, pyrogen free water (milli Q quality) pH=7.2, at about 1 mg/mL concentration, based on the wet weight of the precipitate. The suspension is stored at +4° C. A KDO dosage is achieved to determine the LPS content and the suspension is adjusted to e.g. 0.50 mg/mL of complex (expressed as LPS content).

The LPS-peptide complex tested in the following examples is the LPS-antiparallel dimer complex as obtained in section 4.3, unless otherwise indicated Therefore, this specific complex is simply referred to as LPS-peptide complex.

In a similar manner, the LPS as obtained in section 4.2. is simply referred to as LPS.

Comparison of LPS and LPS-peptide complex is achieved using the LPS lot also used for the preparation of the complex.

EXAMPLE 5

Evaluation of the Detoxification of the LPS-peptide Complex

Several assays are used to evaluate the detoxification.

5.1. Limulus Amebocyte Lysate (LAL) Assay

In this assay, the ability of the SAEP2-L2 anti-parallel and parallel dimers and the SAEP2-L2 cyclic monomer to detoxify LPS is compared. To this end, the LPS-peptide complexes involving the parallel dimer or the monomer are prepared exactly as it is reported in Example 4 for the LPS-antiparallel peptide complex.

LAL is a very sensitive test used to detect and quantify endotoxins of gram-negative bacteria. The test is based on the property of the amoebocyte lysate protein from horseshoe crab (*Limulus polyphemus*) to induce coagulation in the presence of endotoxin.

The evaluation of the LPS endotoxin activity is performed by using the end-point-chromogenic technique, in accordance with the European Pharmacopeia [as described in the European Pharmacopeia techniques (Edition 5.0, paragraph 2.6.14)]. To this end, the kit QCL-1000 ref 50-647 U (Cambrex-BioWhittaker™) is used (linear zone of the kit: 0.1 to 1 Ul/mL) as well as a positive control (*E. coli* endotoxin, 4 $10^3$ EU/mL, Sigma).

Dilution of (i) samples to be tested, (ii) standard and (iii) positive control are achieved with dilution buffer (Cambrex-BioWhittaker™) to cover the respective ranges: 1/10 to $1/10^5$; 0.5 to 0.031 EU/mL and $1/10^4$ to 1.8 $10^4$.

50 μl of sample, standard and positive control dilutions are dispensed per well of 96 flat-bottom well ELISA plate. Fifty μl of lysate are added per well. Incubation is pursued for 10 min at 37° C. Then 100 ill of the p-nitroanlline chromogenic substrate are added. Incubation is pursued for 6 min at 37° C. The chromogenic reaction is stopped while adding 100 μl freezed acetic acid 25% in water. Plate is read by spectrophotometry at 405 nm.

The results are expressed in Endotoxin Unit (EU)/μg of complex. They are shown in the table hereinafter. The detoxification ratio can be established by the LPS/LPS-peptide complex ratio and expressed in log unit.

| | | Mean value | Detoxification ratio | |
|---|---|---|---|---|
| | Range EU/μg | EU/μg | | Expressed in log |
| LPS (6 assays) | 1-12 $10^4$ | 25,000 | | |
| LPS-antiparallel peptide complex (13 assays) | 5-32 | 12-20 | 1,250-2,000 | 3.5 |
| LPS-parallel peptide complex | 30-40 | 30-40 | 600-800 | 3 |
| LPS-monomer peptide complex | >2000 | >2000 | <12.5 | <1 |

As may be seen, the dimeric forms of the SAEP2-L2 peptide are more effective in detoxifying LPS than the cyclic monomer form.

5.2. Pyrogen Test In Rabbits

Rabbit is known to be the animal specie with sensitivity to pyrogenic effects of LPS equivalent to humans. The pyrogen test consists in measuring the rise in body temperature evoked in three rabbits by the intravenous (IV) injection of a sterile solution of the substances to be examined. The test, reading and calculations are performed in accordance with the European Pharmacopoeia, (Edition 5.0, paragraph 2.6.8). The temperature rise is interpreted depending the summed response of the temperatures:conformity is met when the summed response does not exceed 1.15° C.; and non-conformity, when the summed response exceeds 2.65° C. In the present case, the pyrogenic threshold is set up below, between 1.15° C. and 2.65° C.

As found, the limit pyrogen dose (I) in rabbit corresponds to 0.025 ng/kg (LPS), and 10-25 ng/kg (LPS-peptide complex). These results show that the LPS-peptide complex is less pyrogen than LPS, when given by the intravenous route. As measured in this test, the detoxification ratio (LPS-peptide complex/LPS) is between 400 and 1,000.

5.3. Acute Toxicity Assay:LD50 In D-galactosamine Sensitized Mice

References for this assay include i.a Galanos et al, 1979, PNAS 76: 5939 Baumgartner et al, 1990, J. Exp. Med. 171 (3): 889 and U.S. Pat. No. 6,531,131.

Groups of eight-week old female inbred mice are injected by the intraperitoneal (IP) route (0.5 mL) with escalating doses of LPS or LPS-peptide complex, just after being treated with D-galactosamine (15 mg/0.2 mL) by the IP route (the toxicity of LPS is increased of around 1,000 fold with the D-galactosamine treatment which renders the model very sensitive). The death rate is then followed during four days.

The LD50 observed with the LPS is 3.6 ng/mouse (1.91-6.70 ng/mouse); whereas that observed with the LPS-peptide complex is 1 μg/mouse (0.2-5 μg/mouse), indicating that the detoxification ratio (LPS-peptide complex/LPS) is about 250 (100-1000).

5.4. Attenuation of the Pro-inflammatory Effects of LPS when Completed with Peptide In order to evaluate to which extent the LPS-peptide complex can attenuate LPS-induced toxic effects, the effect of the LPS-peptide complex on the release of pro-inflammatory cytokines is monitored (assessed) in in vitro and in vivo assays.

In vivo: cytokine (IL6 and TNFα) releases in the sera of mice immunized either with LPS or LPS-peptide complex are compared by ELISA. Blood samples are recovered 90 min after SC immunization, which is the optimal time for the release of those cytokines. C3H/HeOuJ, TLR4-/-, C3H/HeN and CD1 mouse strains are tested. The two first are sensitive neither to LPS nor LPS-peptide complex. The third and fourth are both found LPS-sensitive. CD1 mice are found more LPS-peptide complex-sensitive than the others and therefore selected for further experiments retaining the most severe conditions.

In vitro:cytokine (IL6, IL8 and TNFα) releases from human whole blood cell cultures stimulated for 24h at 37° C., with different concentrations of LPS or LPS-peptide complex are compared.

5.4.1. In Vivo Assay

CD1 mice are administered subcutaneously (SC) (i) either 10 μg of LPS or (ii) 10 μg of LPS-peptide complex. They are bled 90 minutes after injection. IL6 and TNFα releases are measured in the sera by ELISA.

ELISA Detection of Cytokine Secretion

ELISAs are carried out using the OptEIA mouse IL6 and TNFα sets (Pharmingen), each including the capture antibody (anti-mouse cytokine), the detection antibody (biotinylated anti-mouse cytokine), avidin-horseradish peroxidase conjugate and the standard (recombinant cytokine), all from Pharmingen.

Anti-mouse EL6 and TNFα antibodies are 1/250 diluted in 0.1 M carbonate buffer pH 9.5 (Sigma). For each assay, 100 μl of an antibody dilution are distributed per well of a Maxisorp NUNC 96 flat-bottom well ELISA plate. Plates are incubated overnight at +4° C.

Plates are washed in PBS 0.05% Tween 20. 200 μl of PBS, 0.5% bovine serum albumin (BSA) saturation buffer are then added per well. Incubation is pursued for one hr at room temperature. Plates are washed in PBS 0.05% Tween 20.

Recombinant IL6 or TNFα cytokine dilutions are prepared in the RPMI medium 1% FCS 10%, within the range of (i) 4,000 pg/mL-62.5 pg/mL standard. 100 μl of each dilution are distributed per well, to establish the standard curve.

Serum dilutions are prepared in the RPM' medium P.S. glu 1% FCS 10%. Sera of mice injected with LPS are 1/25 and 1/125 diluted. Sera of mice injected with LPS-peptide complex are 1/5 and 1/25 diluted 100 μl of each dilution are distributed per well.

Incubation is pursued for 2 hrs at room temperature.

Plates are washed in PBS 0.05% Tween 20. Biotinylated anti-mouse cytoline antibodies and the enzyme are each 1/250 diluted in PBS 10% fetal calf serum. 100 μl of each dilution are added per well. Incubation is pursued for one hr at room temperature.

Plates are washed in PBS 0.05% Tween 20. 100 μl of tetramethylbenzidine (TMB) substrate (TMB solutions A and B (KPL) mixed vol/vol) are distributed in wells. Incubation is pursued for 10-30 min at room temperature.

The reaction is stopped by adding 100 μl of 1 M $H_3PO_4$ per well. Plates are read at 450 nm. Results are to be seen in the table hereinafter.

|  | IL6 release | | TNFα release | |
|---|---|---|---|---|
| Product injected to mice | Mean (pg/mL) n = 6 (log) | Detoxification ratio (log unit) | Mean (pg/mL) n = 6 (log) | Detoxification ratio (log unit) |
| LPS | 4.7 | | 4.1 | |
| LPS-peptide complex | 2.2 | 2.5 | <1 | >3.1 |
| Peptide | <1 | | <1 | |

The peptide alone does not induce IL6 or TNFα. The LPS-peptide complex allows for about 100-fold of detoxification (100-fold decrease in IL6 secretion).

5.4.2. In vitro Assay

Preparation of the Test Substances

LPS preparation (1 mg/mL) and LPS-peptide complex (500 μg/mL) are each diluted in 10 mM Tris, NaCl 150 mM, 0.05% Tween 20, 5% sucrose to a concentration of 50 μg/mL. They are further diluted in physiological saline to a concentration of 5 μg/mL.

Serial 1/5 dilutions are performed in AIM-V medium (Gibco (Invitrogen)) for each test substance down to a concentration of $2.56 \cdot 10^{-3}$ pg/mL.

Stimulation

Human blood collected on sodium heparin (25,000 U/5 mL; sanofi-synthelabo) is diluted 1:4 (vol: vol) in AIM-V medium and distributed in Micronics™ tubes (400 μl /tube). 100 μl of a dilution of the test substances are added. Peptide and buffer controls are tested at 1/20 dilution. Tubes are incubated for 24 hrs at 37° C., in a wet atmosphere at 5% $CO_2$.

Plasma Recovery

Tubes are then centrifuged for 10 min at 500 g. At least 200 μl of supernatant are recovered from each tube and kept frozen at −80° C. until titration.

ELISA Detection of Cytokine Secretion

ELISAs are carried out using the OptEIA human IL6, IL8 and TNFα sets from Pharmingen, each including the capture antibody (mouse anti human cytokine), the detection antibody (biotinylated mouse anti-human cytokine), avidin-horseradish peroxidase conjugate and the standard (recombinant cytokine).

Anti-human IL6, IL8 and TNFα antibodies are 1/250 diluted in 0.1 M carbonate buffer pH 9.5 (Sigma). For each assay, 100 μl of an antibody dilution are distributed per well of a Maxisorp NUNC 96 flat-bottom well ELISA plate. Plates are incubated overnight at +4° C.

Plates are washed in PBS 0.65% Tween 20. 200 µl of PBS, 0.5% bovine serum albumin (BSA) saturation buffer are then added per well. Incubation is pursued for one hr at room temperature. Plates are washed in PBS 0.05% Tween 20.

Recombinant IL6, IL8 or TNFα cytokine dilutions are prepared in AIM-V medium within respective range of (i) 1,200 pg/mL-18.75 pg/mL; (ii) 800 pg/mL-12.5 pg/mL; and (iii) 1,000 pg/mL-15.87 pg/mL standard. 100 µl of each dilution are distributed per well, to establish the standard curve.

Plasma dilutions are prepared in the AIM-V. Plasmas recovered from blood stimulated with LPS are 1/25 and 1/125 diluted. Those recovered from blood in contact with the LPS-peptide complex are 1/5 and 1/25 diluted. 100 µl of each dilution are distributed per well.

Incubation is pursued for 2 hrs at room temperature.

Plates are washed in PBS 0.05% Tween 20. Biotinylated anti-human cytokine antibodies and the enzyme are each 1/250 diluted in PBS 10% fetal calf serum. 100 µl of each dilution are added per well. Incubation is pursued for one hr at room temperature.

Plates are washed in PBS 0.05% Tween 20. 100 µl of tetramethylbenzidine (TMB) substrate (TMB solutions A and B (KPL) mixed vol/vol) are distributed in wells. Incubation is pursued for 10-30 min at room temperature.

The reaction is stopped by adding 100 µl of 1 M $H_3PO_4$ per well. Plates are read at 450 mn.

Results

The raw results and the cytokine release curves=f (LPS or complex concentrations) do not allow comparison of different samples. Calculating the detoxification ratio can eliminate inter-blood donor and inter-test variability. Only the linear parts of the curves are taken into account for calculation of the detoxification ratio. The maximum IL6 release beyond which a linear progression is no longer observed is determined and then, the amount of substance required to induced 50% of that maximum is calculated by linear regression.

The detoxification ratio is expressed as the ratio of the concentration of the LPS-peptide complex inducing 50% of maximum IL6 release ($ED_{50}$ expressed in pg/mL) in over that observed with LPS. Higher the ratio, stronger the detoxification is. As the detoxification ratio is systematically measured using whole blood of several independent donors, results are averaged.

The detoxification ratio observed with the LPS-peptide complex is measured several times. Mean data out of six values obtained in the IL6 release assay: 64±20.

The IL6 release correlates with the TNFα and IL8 secretions. Therefore, the IL6 release assay is selected to routinely evaluate the inflammation decrease observed with the LPS-peptide complex.

5.5. Conclusion

The detoxification ratio is measured between $10^2$ and $10^3$, depending on the test. The detoxification values are summarized in the following table.

| Assays | LPS L8 | LPS-peptide complex | Detoxification ratio |
|---|---|---|---|
| LAL | 25,000 EU/µg | 12-20 EU/µg | 1,250-2,000 |
| Limit pyrogen dose (IV) in rabbit | 0.025 ng/kg | 10-25 ng/kg | 400-1,000 |
| Cytokine release test in mice | IL6 = 25,000 pg/mL IL6 = 10,000 pg/mL | IL6 = 270 pg/mL IL6 = 100 pg/mL | 100 |
| In vitro assay of IL6 release by human PBMC ($ED_{50}$: concentration of product inducing 50% of maximum IL6 release) | $ED_{50}$ = 2 pg/mL | $ED_{50}$ = 880 pg/mL | 64 |
| LD50 in galactosamine-sensitized mice | 4 ng/souris | 1 µg/souris (0.2-5) | 250 |

EXAMPLE 6

LPS Peptide Complex Stability Study

The stability of the LPS-peptide complex is studied for 6 months and evaluated by measuring the detoxification ratio in two assays (LAL and in vitro IL-6 release by huPBMC). Pyrogen test in rabbits may also be achieved.

6.1. In vitro Stability of the Formulated LPS Peptide Complex

The stability of the formulated LPS-peptide complex is followed at 5° C., for 6 months. Measurements are made at day=0, 90 and 180 (6 months). Results are as follows.

| IL6 release from human blood cells (detoxification ratio) | | | LAL assay endotoxin (EU/µg) | | | Pyrogen test Pyrogenic threshold, as chosen: 10 ng/mL/kg IV | | |
|---|---|---|---|---|---|---|---|---|
| 0 | 3 months | 6 months | 0 | 3 months | 6 months | 0 | 3 months | 6 months |
| 125 | 40 | 163 | 14 | 58 | 10 | C* | C | C |

C* conform

The detoxification ratio in IL6 release test are not significantly different after 3 and 6 months, indicating the stability of the LPS-peptide complex: LPS complexed with peptide remains detoxified after 6 months at 5° C.

6.2. In vitro Stability of the LPS Peptide Complex in Physiological Liquid

The aim of the experiment is to verify that LPS is not released when the complex is administered and that the detoxification rate does not decrease after a contact with a physiological liquid.

One mL of the LPS-peptide complex, mixed with 1 mL of human serum, is incubated at 37° C. The detoxification rate is evaluated after 1 and 24 hours. Human serum and the LPS-peptide complex as prepared in section 4.3. are also tested in parallel.

No significant difference of the detoxification evaluated by both assays is observed after a 1-hour and 24-hour contact of the LPS-peptide complex with human serum at 37° C. and results are similar to the LPS-peptide complex control.

EXAMPLE 7

Immunogenicity of the LPS-peptide Complex 7.1. Bactericidal Activity of Anti LPS Antibodies Induced In Rabbits By the LPS-peptide Complex Immunization of three adult New-Zealand rabbits is performed with 100 µg of LPS-peptide complex by intramuscular (IM) and subcutaneous (SC) routes (2×0.5 mL and 5×0.2 mL respectively) in the presence of adjuvant. They receive three injections at 3-week interval; the first one with complete Freund adjuvant (FA), the second and third ones with incomplete Freund adjuvant. They are bled two weeks after the last injection. A control group is immunized with the peptide with adjuvant (71 µg, equivalent to the amount of the peptide in 100 µg of LPS-peptide complex) using the same protocol.

The bactericidal activity of the serum (SBA) samples is evaluated against the N. meningitidis strain used for LPS production as described in Example 5 in the presence of baby rabbit serum as exogenous source of complement.

SBA Assay

Sera are heat-inactivated during 30 min at 56° C. In the wells of a 96-well microplate, heat-inactivated sera are then twofold serially diluted (10 times) in Dulbecco's phosphate buffered saline containing $Ca^{++}$ and $Mg^{++}$ (volume per well: 50 µl).

Twenty five µl of a log phase culture of N. meningitidis grown in Mueller-Hinton broth ($4.10^3$ CFU/mL) and 25 µl of baby rabbit serum are added to each well. The plate is incubated one hour at 37° C., under shaking.

Fifty µl of the mixture from each well are plated onto Mueller-Hinton agar. Petri dishes are incubated overnight at +37° C. in a 10% $CO_2$ atmosphere.

In each experiment, controls include (i) bacteria and the complement source without antibodies (complement control), (ii) bacteria and heat-inactivated complement, and (iii) bacteria and heat-inactivated complement, in the presence of antibodies.

Bactericidal titre is reported as the highest reciprocal serum dilution at which ≧50% killing of bacteria is observed as compared to the complement control.

SBA Results

Results are to be seen in the table hereinafter. High SBA titers are obtained with the complex. The specificity of the SBA response is confirmed with the extinction of the response, when the sera (post-dose 3) are adsorbed on LPS.

|  | Rabbit # | Pre-immunized sera | Post-dose 3 immunized sera | Post-dose 3 immunized sera adsorbed on LPS |
|---|---|---|---|---|
| LPS-peptide complex | A | 16 | 512 | 4 |
|  | B | 16 | 1,024 | 8 |
|  | C | 4 | 128 | <4 |
| Peptide | D | 4 | 16 | 4 |
|  | E | 16 | 16 | 8 |

7.2. Immune Response Induced in Mice with the LPS-peptide Complex

Ten six-week old female outbred CD1 mice are immunized with a 10 µg dose of LPS-peptide complex by the subcutaneous route (0.2 mL). They receive two injections at 3-week interval. They are bled before each injection and exsanguinated 14 days after the last injection. A control group is injected with buffer.

In a first experiment, the antibody response is evaluated by ELISA and the bactericidal activity of the post-dose 2 serum samples is evaluated against the N. meningitidis strain used for LPS production as described in Example 4 (homologous strain) and a heterologous N. meningitidis strain [N. meningitidis group B strain RH873 (L4, 7, 8 immunotype)].

In a second experiment, the antibody response is evaluated by ELISA and the opsonic activity of the post-dose 2 serum samples is evaluated by FACS.

7.2.1. Immunogenicity of LPS-peptide Complex in Mice

ELISA Titration of Anti-LPS Antibodies

Wells of a 96-well microplate are coated with 100 µl of a 10 µg/mL LPS solution in buffer 1 (PBS+10 mM $MgCl_2$). The plate is incubated 2 hours at +37° C.; then overnight at +5° C.

The LPS solution is removed from the plate and wells are saturated with 150 µl of buffer 2 (PBS+milk 1% +Tween 20 0.05%). The plate is incubated one hour at 37° C.; then washed with buffer 3(PBS+Tween 20 0.05%).

Sera are serially diluted 12-fold, directly in the wells using buffer 2 (volume: 100 µl per well). The plate is incubated for 90 min at +37° C.; then washed with buffer 3.

Hundred µl of a diluted goat anti-mouse IgG (γ chain specific) or IgM (µ chain specific) peroxydase conjugate are added in each well. The plate is incubated 90 min at 37° C. and then washed with buffer 3.

The reaction is developed by adding 100 µl of a tetramethylbenzidine substrate solution in each well. The plate is incubated 20 min at 37° C. The reaction is stopped by adding 1 M HCl and absorbance is measured at 450 mn.

ELISA Results

Results are expressed in arbitrary ELISA Unit/mL (EU/mL) by comparison to a reference serum.

In a preliminary immunization experiment, the ELISA assay is achieved using a pool of sera. As shown in the following table, the LPS-peptide complex is able to induce high anti-LPS IgG titers in mice and anti-LPS IgM after one injection (ELISA). A significant IgG booster is observed after the second injection, whereas no significant IgM increase is observed.

|  | Anti-LPS IgG (EU/mL) | | Anti-LPS IgM (EU/mL) | |
| --- | --- | --- | --- | --- |
|  | Post dose 1 | Post dose 2 | Post dose 1 | Post dose 2 |
| LPS-peptide complex | 1,800 | 22,000 | 280 | 550 |
| Buffer | <40 | <40 | <40 | <40 |

In a further imunisation experiment, the ELISA assay is achieved individually. After the second injection, seven out of the ten mice exhibits high IgG and IgM titers. Global mean titers expressed in log are about 3.7 and 2.8 respectively.

7.2.2. Bactericidal Activity of Mouse Sera

Bactericidal activity is measured as described in section 7.1.

Fourty % of the post-dose 2 sera exhibit a bactericidal activity (SBA titre ≧16) against the homologous *N. meningitidis* strain. Four are bactericidal against the heterologous strain.

7.2.3. Opsonic Activity of Mouse Sera

Opsonisation Assay

The opsonic activity is measured by flow cytometry technology (FACS) using human promyelocytic differentiated HL60 cells as effector and LPS coated latex fluorescent beads as target.

Effector cells are differentiated into granulocytes after treatment with 100 mM dimethylformamide. The resulting cells are washed, resuspended in Hanks' balanced salt solution and their concentration is adjusted to $2.5 \times 10^7$ cells/mL.

Sera are heat inactivated during 30 min at 56° C. In a 96 deep-well microplate, heat-inactivated sera are serially five-fold diluted (3 times) in Hanks balanced salt buffer containing Ca++ and Mg++ (volume per well: 300 µl).

Twenty µl of LPS coated latex fluorescent beads and 10 µl of baby rabbit serum as exogenous complement source are added to each well. The plate is incubated 30 min at +37° C., under shaking.

Fifty µl of the effector cell suspension are added to each well. The plate is incubated 30 min at +37° C., under shaking.

One hundred fifty µl from each well are transferred in a second deep well and the reaction is stopped by adding 400 µl of PBS+0.02% EDTA. The plate is centrifuged and washed twice with PBS+BSA buffer.

The phagocytosis of LPS coated beads by effector cells, in the presence of antiserum and exogenous complement source is measured by FACS.

Opsonic activity is expressed as the inverse of serum dilution giving a phagocytosis product (PP)=200. PP is measured as the ratio number of beads/phagocytic cells × number of fluorescent cells.

Controls wells lacking antiserum and a positive monoclonal antiserum are included in each experiment.

Opsonisation Results

Eight out of ten mice exhibit high opsonic activity (≧350).

The invention claimed is:

1. A SAEP II peptide dimer, wherein the peptide dimer is essentially in the form of (a) a dimer of formula (I)

NH$_2$-A-Cys1-B-Cys2-C—COOH

NH$_2$-A'-Cys1-B'-Cys2-C'—COOH wherein Cys1 and Cys2 are each a cysteine amino acid;
wherein the two Cys1 residues are linked together through a disulphide bond and the two Cys2 residues are linked together through a disulphide bond;
and/or (b) a dimer of formula (II)

NH$_2$-A-Cys1-B-Cys2-C—COOH

HOOC—C'-Cys2-B'-Cys1-A'-NH$_2$ wherein Cys1 and Cys2 are each a cysteine amino acid;
wherein the Cys1 residues are linked to the Cys2 residues through intermolecular disulphide bonds;
wherein A and A' independently are a peptide moiety of from 2 to 5 amino acid residues, in which at least 2 amino acid residues are independently selected from Lys, Hyl (hydroxy-Lysine), Arg and His;
wherein B and B' independently are a peptide moiety of from 3 to 7 amino acid residues, which comprise at least two amino acid residues independently selected from Val, Leu, Ile, Phe, Tyr and Trp; and
wherein C and C' are optional and are independently an amino acid residue or a peptide moiety of from 2 to 3 amino acid residues;
provided that the cationic amino acid residues/hydrophobic amino acid residues ratio (cat/hydroph ratio) of the dimer is from 0.4 to 2.

2. The SAEP II peptide dimer according to claim 1, wherein the cat/hydroph ratio is from 0.5 to 1.5.

3. The SAEP II peptide dimer according to claim 2, wherein the cat/hydroph ratio is from 0.6 to 1.

4. The SAEP II peptide dimer according to claim 3, wherein the cat/hydroph ratio is from 0.6 to 0.8.

5. The SAEP II peptide dimer according to claim 1, wherein the B and B' peptide moieties comprise the sequence -X1-X2-X3-, in which X1 and X2; X2 and X3; or X1, X2 and X3 are independently selected from Val, Leu, Ile, Phe, Tyr and Trp.

6. The SAEP II peptide dimer according to claim 5, wherein the B and B' peptide moieties independently comprise:

(i) the sequence -X1-X2-X3-, in which:
   X1 is Lys, Hyl, His or Arg;
   X2 is Phe, Leu, Ile, Tyr, Trp or Val; and
   X3 is Phe, Leu, Ile, Tyr, Trp or Val; and
(ii) if the B and B' peptide moieties comprise amino acid residues, in addition to the sequence -X1-X2-X3-, the additional amino acid residues are independently selected from the group consisting of Val, Leu, Ile, Phe, Tyr, Trp, Lys, Hyl, Arg and His.

7. The SAEP II peptide dimer according to claim 1, which is a dimer of formula (III)

NH$_2$-A-Cys1-B-Cys2-COOH

NH$_2$-A'-Cys1-B'-Cys2-COOH wherein the two Cys1 residues are linked together through a disulphide bond and the two Cys2 residues are linked together through a disulphide bond;
and/or formula (IV)

NH$_2$-A-Cys1-B-Cys2-COOH

HOOC-Cys2-B'-Cys1-A'-NH$_2$, wherein the Cys1 residues are linked to the Cys2 residues through intermolecular disulphide bonds.

8. The SAEP II peptide dimer according to claim 1, which is a homologous peptide dimer.

9. The SAEP II peptide dimer according to claim 1, which is an antiparallel dimer form of formula (VI)

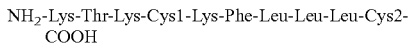
NH$_2$-Lys-Thr-Lys-Cys1-Lys-Phe-Leu-Leu-Leu-Cys2-COOH

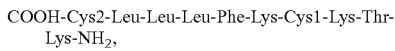
COOH-Cys2-Leu-Leu-Leu-Phe-Lys-Cys1-Lys-Thr-Lys-NH$_2$, wherein the Cys1 residues are linked to the Cys2 residues through intermolecular disulphide bonds.

10. The SAEP II peptide dimer according to claim 1, which is a parallel dimer of formula (VII)

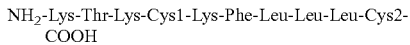
NH$_2$-Lys-Thr-Lys-Cys1-Lys-Phe-Leu-Leu-Leu-Cys2-COOH

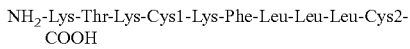
NH$_2$-Lys-Thr-Lys-Cys1-Lys-Phe-Leu-Leu-Leu-Cys2-COOH wherein the two Cys1 residues are linked together through a disulphide bond and the two Cys2 residues are linked together through a disulphide bond.

11. A composition comprising a peptide dimer according to claim 1, wherein the peptide dimer is essentially in dimeric parallel form.

12. A composition comprising a peptide dimer according to claim 1, wherein the peptide dimer is essentially in dimeric antiparallel form.

13. A pharmaceutical composition comprising (i) a peptide dimer according to claim 1 and (ii) a pharmaceutically acceptable diluent or carrier.

14. A method for treating or preventing septic shock, which comprises administering a therapeutically effective amount of a peptide dimer according to claim 1 to an individual in need.

15. A LPS-peptide complex comprising (i) a LPS entity of Gram-negative bacteria and (ii) a SAEP II peptide dimer according to claim 1, wherein the LPS moiety and the SAEP II peptide are non-covalently bound to each other.

16. The LPS-peptide complex according to claim 15, in which the LPS is a LPS of *N. meningitidis*; *E. coli*; *Salmonella typhi*; *Salmonella paratyphi*; *Shigella fexneri*; *Haemophilus influenzae*, *Helicobacter pylori*; *Chlamydia trachomatis*; *Bordetella pertussis*; *Brucella*; *Legionella pneumophia*; *Vibrio cholera*; *Moraxella catharralis*; *Pseudomonas aeruginosa*; and *Klebsiella pneumonia*.

17. The LPS-peptide complex according to claim 16, in which the LPS is a LPS of *Neisseria meningitidis*.

18. The LPS-peptide complex according to claim 17, in which the LPS is LPS L8.

19. The LPS-peptide complex according to claim 17, characterized by a molar LPS:peptide ratio of from 1:1.5 to 1:0.5.

20. The LPS-peptide complex according to claim 19, characterized by a molar LPS:peptide ratio of 1:1.

21. A pharmaceutical composition comprising a LPS-peptide complex according to claim 15, and a pharmaceutically acceptable diluent or carrier.

22. A method for treating or preventing a Gram-negative bacterial infection, which comprises administering a therapeutically effective amount of a LPS-peptide complex according to claim 15, to an individual in need thereof.

23. A process for preparing a LPS/peptide complex, which comprises mixing together (i) a LPS of Gram-negative bacteria and (ii) a peptide dimer according to claim 1.

24. The process according to claim 23, wherein the LPS and the peptide dimer or salt thereof are mixed in a molar LPS:peptide ratio of from 1:1.2 to 1:0.8.

25. The process according to claim 24, wherein the LPS and the peptide dimer or salt thereof are mixed in a 1:1 molar LPS:peptide ratio.

26. A process for detoxifying a LPS of Gram-negative bacteria, which comprises mixing together (i) the LPS and (ii) a peptide dimer according to claim 1.

27. The process according to claim 26, wherein the LPS and the peptide dimer are mixed in a molar LPS:peptide ratio of from 1:1.2 to 1:0.8.

28. The process according to claim 27, wherein the LPS and the peptide dimer or salt thereof are mixed in a 1:1 molar LPS:peptide ratio.

29. The SAEP II peptide dimer according to claim 1, wherein the dimer is purified from non-dimer peptides.

30. The SAEP II peptide dimer according to claim 1, wherein B and B' comprise at least three amino acid residues independently selected from Val, Leu, Ile, Phe, Tyr and Trp.

31. The SAEP II peptide dimer according to claim 30, wherein the dimer is purified from non-dimer peptides.

32. A SAEP II peptide dimer, wherein the peptide dimer is at least 95% in the form of (a) a dimer of formula (I)

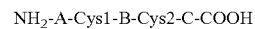
NH$_2$-A-Cys1-B-Cys2-C-COOH

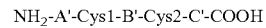
NH$_2$-A'-Cys1-B'-Cys2-C'-COOH wherein Cys1 and Cys2 are each a cysteine amino acid;

wherein the two Cys1 residues are linked together through a disulphide bond and the two Cys2 residues are linked together through a disulphide bond;

and/or (b) a dimer of formula (II)

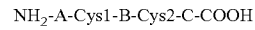
NH$_2$-A-Cys1-B-Cys2-C-COOH

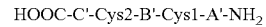
HOOC-C'-Cys2-B'-Cys1-A'-NH$_2$ wherein Cys1 and Cys2 are each a cysteine amino acid;

wherein the Cys1 residues are linked to the Cys2 residues through intermolecular disulphide bonds;

wherein A and A' independently are a peptide moiety of from 2 to 5 amino acid residues, in which at least 2 amino acid residues are independently selected from Lys, Hyl (hydroxy-Lysine), Arg and His;

wherein B and B' independently are a peptide moiety of from 3 to 7 amino acid residues, which comprise at least two amino acid residues independently selected from Val, Leu, Ile, Phe, Tyr and Trp; and wherein C and C' are optional and are independently an amino acid residue or a peptide moiety of from 2 to 3 amino acid residues;

provided that the cationic amino acid residues/hydrophobic amino acid residues ratio (cat/hydroph ratio) of the dimer is from 0.4 to 2.

33. The SAEP II peptide dimer according to claim 32, wherein the cat/hydroph ratio is from 0.5 to 1.5.

34. The SAEP II peptide dimer according to claim 33, wherein the cat/hydroph ratio is from 0.6 to 1.

35. The SAEP II peptide dimer according to claim 34, wherein the cat/hydroph ratio is from 0.6 to 0.8.

36. The SAEP II peptide dimer according to claim 32, wherein the B and B' peptide moieties comprise the sequence -X1-X2-X3-, in which X1 and X2; X2 and X3; or X1, X2 and X3 are independently selected from Val, Leu, Ile, Phe, Tyr and Trp.

37. The SAEP II peptide dimer according to claim 36, wherein the B and B' peptide moieties comprise:
(i) the sequence -X1-X2-X3-, in which:
X1 is Lys, Hyl, His or Arg;
X2 is Phe, Leu, Ile, Tyr, Trp or Val; and
X3 is Phe, Leu, Ile, Tyr, Trp or Val; and
(ii) if the B and B' peptide moieties comprise amino acid residues, in addition to the seciuence -X1-X2-X3-, the additional amino acid residues are independently selected from the group consisting of Val, Leu, Ile, Phe, Tyr, Trp, Lys, Hyl, Arg and His.

38. The SAEP II peptide dimer according to claim 32, which is a dimer of formula (III)

NH$_2$-A-Cys1-B-Cys2-COOH

NH$_2$-A'-Cys1-B'-Cys2-COOH wherein the two Cys1 residues are linked together through a disulphide bond and the two Cys2 residues are linked together through a disulphide bond; and/or formula (IV)

NH$_2$-A-Cys1-B-Cys2-COOH

HOOC-Cys2-B'-Cys1-A'-NH$_2$, wherein the Cys1 residues are linked to the Cys2 residues through intermolecular disulphide bonds.

39. The SAEP II peptide dimer according to claim 32, which is a homologous peptide dimer.

40. The SAEP II peptide dimer according to claim 32, which is an antiparallel dimer form of formula (VI)

NH$_2$-Lys-Thr-Lys-Cys1-Lys-Phe-Leu-Leu-Leu-Cys2-COOH

COOH-Cys2-Leu-Leu-Leu-Phe-Lys-Cys1-Lys -Thr-Lys-NH$_2$, wherein the Cys1 residues are linked to the Cys2 residues through intermolecular disulphide bonds.

41. The SAEP II peptide dimer according to claim 32, which is a parallel dimer of formula (VII)

NH$_2$-Lys-Thr-Lys-Cys1-Lys-Phe-Leu-Leu-Leu-Cys2-COOH

NH$_2$-Lys-Thr-Lys-Cys1-Lys-Phe-Leu-Leu-Leu-Cys2-COOH wherein the two Cys1 residues are linked together through a disulphide bond and the two Cys2 residues are linked together through a disulphide bond.

42. A composition comprising a peptide dimer according to claim 32, wherein the peptide is essentially in dimeric parallel form.

43. A composition comprising a peptide dimer according to claim 32, wherein the peptide is essentially in dimeric antiparallel form.

44. A pharmaceutical composition comprising (i) a peptide dimer according to claim 32 and (ii) a pharmaceutically acceptable diluent or carrier.

45. A SAEP II peptide dimer, wherein the peptide is essentially in the form of
(a) a dimer of-formula (I)

NH$_2$-A-Cys1-B-Cys2-C-COOH

NH$_2$-A'-Cys1-B'-Cys2-C'-COOH wherein Cys1 and Cys2 are each a cysteine amino acid;
wherein the two Cys1 residues are linked together through a disulphide bond and the two Cys2 residues are linked together through a disulphide bond;

and/or
(b) a dimer of formula (II)

NH$_2$-A-Cys1-B-Cys2-C-COOH

HOOC-C'-Cys2-B'-Cys1-A'-NH$_2$ wherein Cys1 and Cys2 are each a cysteine amino acid;
wherein the Cys1 residues are linked to the Cys2 residues through intermolecular disulphide bonds;
wherein A and A' independently are a peptide moiety of from 2 to 5 amino acid residues, in which at least 2 amino acid residues are independently selected from Lys, Hyl (hydroxy-Lysine), Arg and His;
wherein B and B' independently are a peptide moiety of from 3 to 7 amino acid residues, which comprise at least two amino acid residues independently selected from Val, Leu, Ile, Phe, Tyr and Trp; and
wherein C and C' are optional and are independently an amino acid residue or a peptide moiety of from 2 to 3 amino acid residues;
provided that the cationic amino acid residues/hydrophobic amino acid residues ratio (cat/hydroph ratio) of the dimer is from 0.4 to 2, and
wherein the dimer is in solid form.

46. A pharmaceutical composition comprising (i) a peptide dimer according to claim 45 and (ii) a pharmaceutically acceptable diluent or carrier.

47. The SAEP II peptide dimer according to any one of claims 1 or 32, which is a heterodimer.

48. A LPS-peptide complex comprising (i) a LPS entity (moiety) of Gram-negative bacteria and (ii) a SAEP II peptide dimer according to claim 32, wherein the LPS moiety and the SAEP II peptide are non-covalently bound to each other.

49. The LPS-peptide complex according to claim 48, in which the LPS is a LPS of *N. meningitidis; E. coli; Salmonella typhi; Salmonella paratyphi; Shigella fexneri; Haemophilus influenzae; Helicobacter pylori; Chlamydia trachomatis; Bordetella pertussis; Brucella; Legionella pneumophia; Vibrio cholera; Moraxella catharralis; Pseudomonas aeruginos;* and *Kiebsiella pneumonia.*

50. The LPS-peptide complex according to claim 49, in which the LPS is a LPS of *Neisseria meningitidis.*

51. The LPS-peptide complex according to claim 50, in which the LPS is LPS L8.

52. The LPS-peptide complex according to claim 50, characterized by a molar LPS:peptide ratio of from 1:1.5 to 1:0.5.

53. The LPS-peptide complex according to claim 52, characterized by a molar LPS:peptide ratio of 1:1.

54. A pharmaceutical composition comprising a LPS-peptide complex according to claim 48, and a pharmaceutically acceptable diluent or carrier.

55. A process for preparing a LPS/peptide complex, which comprises mixing together (i) a LPS of Gram-negative bacteria and (ii) a peptide dimer according to claim 32.

56. The process according to claim 55, wherein the LPS and the peptide dimer or salt thereof are mixed in a molar LPS:peptide ratio of from 1:1.2 to 1:0.8.

57. The process according to claim 56, wherein the LPS and the peptide dimer or salt thereof are mixed in a 1:1 molar LPS:peptide ratio.

58. A LPS-peptide complex comprising (i) a LPS entity (moiety) of Gram-negative bacteria and (ii) a SAEP II peptide dimer according to claim 9, wherein the LPS moiety and the SAEP II peptide are non-covalently bound to each other.

59. The LPS-peptide complex according to claim 58, in which the LPS is a LPS of *N. meningitidis; E. coli; Salmonella typhi; Salmonella paratyphi; Shingella fexneri; Hae-*

*mophilus influenzae; Helicobacter pylori; Chlamydia trachomatis; Bordetella pertussis; Brucella; Legionella pneumophia; Vibrio cholera; Moraxella catharralis; Pseudomonas aeruginosa;* and *Kiebsiella pneumonia.*

60. The LPS-peptide complex according to claim 59, in which the LPS is a LPS of *Neisseria meningitidis.*

61. The LPS-peptide complex according to claim 60, in which the LPS is LPS L8.

62. The LPS-peptide complex according to claim 60, characterized by a molar LPS:peptide ratio of from 1:1.5 to 1:0.5.

63. The LPS-peptide complex according to claim 62, characterized by a molar LPS:peptide ratio of 1:1.

64. A pharmaceutical composition comprising a LPS-peptide complex according to claim 58, and a pharmaceutically acceptable diluent or carrier.

65. A process for preparing a LPS/peptide complex, which comprises mixing together (i) a LPS of Gram-negative bacteria and (ii) a peptide dimer according to claim 9.

66. The process according to claim 65, wherein the LPS and the peptide dimer or salt thereof are mixed in a molar LPS:peptide ratio of from 1:1.2 to 1:0.8.

67. The process according to claim 66, wherein the LPS and the peptide dimer or salt thereof are mixed in a 1:1 molar LPS:peptide ratio.

68. A LPS-peptide complex comprising (i) a LPS entity (moiety) of Gram-negative bacteria and (ii) a SAEP II peptide according to claim 40, wherein the LPS moiety and the SAEP II peptide dimer are non-covalently bound to each other.

69. The LPS-peptide complex according to claim 68, in which the LPS is a LPS of *N. meningitidis; E. coli; Salmonella typhi; Salmonella paratyphi; Shingella fexneri; Haemophilus influenzae; Helicobacter pylori; Chlamydia trachomatis; Bordetella pertussis; Brucella; Legionella pneumophia, Vibrio cholera, Moraxella catharralis, Pseudomonas aeruginosa,* and *Kiebsiella pneumonia.*

70. The LPS-peptide complex according to claim 69, in which the LPS is a LPS of *Neisseria meningitidis.*

71. The LPS-peptide complex according to claim 70, in which the LPS is LPS L8.

72. The LPS-peptide complex according to claim 70, characterized by a molar LPS:peptide ratio of from 1:1.5 to 1:0.5.

73. The LPS-peptide complex according to claim 72, characterized by a molar LPS:peptide ratio of 1:1.

74. A pharmaceutical composition comprising a LPS-peptide complex according to claim 68, and a pharmaceutically acceptable diluent or carrier.

75. A process for preparing a LPS/peptide complex, which comprises mixing together (i) a LPS of Gram-negative bacteria and (ii) a peptide dimer according to claim 40.

76. The process according to claim 75, wherein the LPS and the peptide dimer or salt thereof are mixed in a molar LPS:peptide ratio of from 1:1.2 to 1:0.8.

77. The process according to claim 76, wherein the LPS and the peptide dimer or salt thereof are mixed in a 1:1 molar LPS:peptide ratio.

* * * * *